United States Patent [19]
Slovacek et al.

[11] Patent Number: 5,863,460
[45] Date of Patent: Jan. 26, 1999

[54] OXYGEN SENSING MEMBRANES AND METHODS OF MAKING SAME

[75] Inventors: Rudolf E. Slovacek, Norfolk; Kevin J. Sullivan, Medfield, both of Mass.

[73] Assignee: Chiron Diagnostics Corporation, E. Walpole, Mass.

[21] Appl. No.: 617,714

[22] Filed: Apr. 1, 1996

[51] Int. Cl.$^6$ ............................ G01N 33/00; G01N 21/64
[52] U.S. Cl. ................... 252/301.35; 436/136; 436/135; 436/172; 422/82.06; 422/82.07; 422/82.09
[58] Field of Search .................................. 436/136, 138, 436/172; 422/82.06, 82.07, 82.08; 252/301.35

[56] References Cited

U.S. PATENT DOCUMENTS

| | | | |
|---|---|---|---|
| 4,476,870 | 10/1984 | Peterson et al. | 128/634 |
| 4,587,101 | 5/1986 | Marsoner et al. | 422/56 |
| 4,716,363 | 12/1987 | Dukes et al. | 324/77 |
| 4,752,115 | 6/1988 | Murray et al. | 350/96.29 |
| 4,810,655 | 3/1989 | Khalil et al. | 436/138 |
| 4,857,472 | 8/1989 | Wolfbeis | 436/122 |
| 4,861,727 | 8/1989 | Hauenstein et al. | 436/136 |
| 5,030,420 | 7/1991 | Bacon et al. | 422/82.07 |
| 5,043,286 | 8/1991 | Khalil et al. | 435/136 |
| 5,047,350 | 9/1991 | Switalski et al. | 436/136 |
| 5,127,405 | 7/1992 | Alcala et al. | 128/633 |
| 5,173,432 | 12/1992 | Lefkowitz et al. | 436/138 |
| 5,190,729 | 3/1993 | Hauenstein et al. | 422/98 |
| 5,387,329 | 2/1995 | Foos et al. | 204/415 |
| 5,462,879 | 10/1995 | Bentsen | 436/136 |
| 5,624,847 | 4/1997 | Lakowicz et al. | 436/68 |

FOREIGN PATENT DOCUMENTS

| | | |
|---|---|---|
| 105870 | 10/1983 | European Pat. Off. . |
| 442 276 A1 | 8/1991 | European Pat. Off. . |
| 0105870 | 4/1994 | European Pat. Off. . |
| WO 90/07107 | 6/1990 | WIPO . |
| WO 92/19957 | 11/1992 | WIPO . |

OTHER PUBLICATIONS

Von H. Kautsky & A. Hirsch; "Nachweis geringster Sauerstoffmengen durch Phosphoreszenztilgunt"; Chemie.Band 222; (1931) 126–134 (German) No Month.

Von H. Kautsky & G.O. Moller; "Luminescenzumwandlung durch Sauerstoff Nachweis geringster Sauerstoffmengen"; Chem.222; (1935) 167–172 (German) No Month.

Von O. Stern & M. Volner; "Uber die Abklingungszeit der Fluoreszenz"; Physik Zeitschr XX; (1919); 183–188 (German) No Month.

D.B. Papkovsky et al; "Phosphorescent polymer films for optical oxygen sensors"; Biosensors & Bioelectronics 7; (1991); 199–206 No Month.

J.N. Demas & B.A. DeGraff; Design and Applications of Highly Luminescent Transition Metal Complexes; Analytical Chemistry, vol. 63, No. 17; (1991); 829–837 No Month.

J. Brandrup & E.H. Immergut; "Polymer Handbook; 3rd Edition"; John Wiley & Sons; New York; NY; (1989); VI435–VI449 No Month.

M. Salame; "Transport properties of nitrile polymers"; J. Polymer Sci. Symp.41; (1973); 1–15 No Month.

(List continued on next page.)

*Primary Examiner*—Melissa Bonner
*Attorney, Agent, or Firm*—Arthur S. Morgenstern; Charles L. Gagnebin, III; Robert P. Blackburn

[57] ABSTRACT

A polymeric sensing membrane having a Stern-Volmer constant within a pre-determined range of Stern-Volmer constants. The membrane includes a polymeric material having a fluorescent dye molecule dispersed therein. The dye molecule is capable of having its fluorescence collisionally quenched by a gas to be detected by the membrane. In one embodiment, the membrane includes a fluorescent dye molecule which has a relaxation time and a polymeric material having a permeability within a range of permeabilities defined by a mathematical function of the pre-determined range of Stern-Volmer constants. In another embodiment, the membrane includes a polymeric having a permeability and a fluorescent dye molecule having a relaxation time within a range of relaxation times defined by a mathematical function of the pre-determined range of Stern-Volmer constants.

20 Claims, 8 Drawing Sheets

OTHER PUBLICATIONS

W.H. Yang, V.F. Smolen & N.A. Peppas; "Oxygen permeability coefficients of polymers for hard and soft contact lens applications"; J. Membr. Sci. 9; (1981); 53–67 No Month.

R.J. Watts & G.A. Crosby; "Spectroscopic characterization of complexes of ruthemium and iridium with 4,4–diphenyl–2, 2–bipyridine and 4, 7–diphenyl–1, 10–phenanthroline"; J.Am.Chem Soc. 93 (1971); 3184–3188 No Month.

T.J. Aartsuma et al; "Porphyrins.43. Triplet sublevel emission of platinum tetrabenzoporphyrin by spectrothermal principal component decomposition"; J.Am.Chem.Soc. 104; (1982) 6278–6283 No Month.

Lui, Hsue–Yang et al., "Oxygen Permeability of Sol–Gel Coatings", *Applied Spectroscopy,* vol. 46, No. 8 (1992), pp. 1266–1272. No Month.

FIG.1 OXYGEN PERMEATION MEMBRANE TEST APPARATUS

OXYGEN PERMEABILITY MEASUREMENTS:
LIQUID/MEMBRANE/LIQUID CONFIGURATION

OXYGEN SENSING MEMBRANES AND METHODS OF MAKING SAME

FIELD OF THE INVENTION

The present invention relates generally to polymeric sensing membranes and ore particularly to such membranes which have a predetermined range of Stern-Volmer constants and methods of making same.

DISCUSSION OF THE RELATED ART

The ability to monitor the concentration of a gas is advantageous in a variety of situations. For example, reactions carried out on a large scale in the chemical industry, such as fermentation reactions, can require the measurement of certain reactant or product gases. In addition, in medical care, continuous monitoring of the respiratory gases is becoming a common procedure for the study of respiration, assisting in anesthesiology and the treatment and diagnosis of cardiopulmonary disorders. In particular, it is often desirable to be able to monitor the level of oxygen in blood using in vitro methods.

One approach to measuring oxygen levels in blood is to use an oxygen sensitive fluorescent membrane. Such membranes typically are comprised of a polymeric material and a fluorescent dye molecule dispersed within the polymeric material. The fluorescent dye molecule is capable of emitting fluorescence which can be collissionally quenched by molecular oxygen. This process is commonly known as Stern-Volmer quenching and is described by the relationship $$F_O/F = \tau_O/\tau = 1 + \tau_O \cdot k_q[O_2] \qquad (1)$$

where $F_O$ and $\tau_O$ are the fluorescence intensity and the relaxation time for the fluorescent dye in the absence of molecular oxygen, F and $\tau$ are the fluorescence intensity and the relaxation time when the molecular oxygen concentration $[O_2]$ is greater than zero, and $k_q$ is the quenching constant for the fluorescent dye molecule. This equation is often rewritten in the form $$F_O/F = \tau_O/\tau = 1 + k_{SV} \cdot pO_2 \qquad (2)$$

where $k_{SV}$ is the Stern-Volmer constant and $pO_2$ is the partial pressure of oxygen. For the application described here, partial pressures are given in units of mmHg where one mmHg is equivalent to one torr. The Stern-Volmer constant is by definition given in units of $(\text{mmHg})^{-1}$ or $\text{torr}^{-1}$.

The method of using oxygen sensitive membranes includes exposing the membrane to electromagnetic radiation capable of exciting the fluorescent dye molecule from the ground electronic state to an excited electronic state. The fluorescent dye molecules then undergo a transition from the excited electronic state back to the ground electronic state while emitting fluorescence at a characteristic wavelength. The amount of oxygen in blood can be determined by measuring the change in certain properties of the fluorescence emitted by the fluorescent dye molecule in the absence of oxygen and in the presence of oxygen.

Several different techniques exist which are designed to measure fluorescence emission properties of fluorescent dye molecules dispersed within polymeric materials. For example, U.S. Pat. Nos. 4,810,655; 4,861,727 and 5,190,729 disclose methods of measuring the time resolved fluorescence emission of a fluorescent dye molecule dispersed within a polymeric material. In addition, U.S. Pat. Nos. 4,716,363; 5,127,405 and WO Patent Application No. 92/19957 disclose a measurement of the phase shift of the fluorescence emitted by a fluorescent dye molecule using a modulated excitation source.

If a pulse of light used to excite a fluorescent dye molecule is of a relatively short duration ($t<<\tau$), the decay of emission intensity from the initial value $F_i$ will be approximately described by $$F(t) = F_i \cdot e^{-t/\tau} \qquad (3)$$

and various sampling and regression schemes can be used to estimate a value for $\tau$.

Alternatively, the excitation signal can be modulated such that the intensity varies sinusoidally $$E(t) = E_p \cdot \left( \frac{1 + \sin \omega t}{2} \right) \qquad (4)$$

where $E_p$ is the peak fluorescence intensity and $\omega$ is the angular frequency of the excitation signal. The fluorescence emission F(t) signal will vary sinusoidally at the same frequency as the excitation signal with a phase lag related to the relaxation time $$F(t) = \frac{1}{(1 - \omega\tau^2)^{1/2}} \cdot F_p \cdot \left( \frac{1 + \sin(\omega t - \phi)}{2} \right) \qquad (5)$$

where $F_p$ is the luminescence intensity that would result from a constant excitation at intensity $E_p$ and $\Phi$ is the phase lag. The relaxation time can be calculated from the observed phase lag using the equation $$\tau = \frac{1}{\omega} \cdot \tan\phi \qquad (6)$$

U.S. Pat. No. 4,716,363 discloses a constant phase method for extracting relaxation information from samples using a variable frequency modulated source. This constant phase technique includes adjusting the frequency (f) of the modulated excitation source with a feedback loop so that a constant phase lag, preferably in the range of 45 degrees, is maintained. A rearrangement of equation (6) and substitution of $\omega = 2\pi f$ yields:

$$f = \tan\phi / (2\pi\tau) \qquad (7)$$

If $\phi$ is held constant at 45 degrees, then tan $\phi = 1$, and by substituting $\tau$ from equation (2), it can be shown that:

$$f = (1 + k_{SV} \cdot pO_2) / 2\pi\tau_O \qquad (8)$$

Thus, the operating frequency of the feedback loop is directly proportional to the partial pressure of oxygen, so the constant phase method provides several advantages over the time resolved and constant frequency methods. For example, the constant phase method significantly reduces the complexity of the calculations required to produce a reported result. In addition, maintaining a constant phase lag permits the phase detector to operate in the most sensitive part of the response curve and optimizes signal to noise ratios by maintaining a constant signal amplitude over a wide range of oxygen partial pressures.

Many different polymeric material/ fluorescent dye molecule systems have been used to make oxygen sensing membranes. For example, U.S. Pat. No. 5,030,420 and *Anal. Chem.* 63, 337 (1991) disclose ruthenium complexes which undergo Stern-Volmer quenching by oxygen. Other fluorescent dye molecules, such as porphyrin derivatives, are disclosed in U.S. Pat. Nos. 4,810,655 and 5,043,286 as well as *Biosensors and Bioelectronics* 7, 199 (1991). In addition, lanthinide complexes used for oxygen sensing are disclosed in U.S. Pat. Nos. 5,190,729 and 4,861,727.

There are relatively few examples of attempts to provide general teachings regarding the selection of appropriate polymeric materials and fluorescent dye molecules for particular sensing membrane applications, and, of the attempts that have been made, there has been only limited success in producing a reliable, membrane.

Because of the lack of such a method, sensing membranes have been made using available polymeric materials and fluorescent dye molecules without being able to design polymeric materials or fluorescent dye molecules for specific applications. Therefore, those skilled in the art often formulate polymeric sensing membranes including polymeric materials and fluorescent dye molecules which have Stern-Volmer constants by an arbitrary formulation and later test to determine if useful values are obtained. If not, an adjusted formulation, which often includes relatively high amounts of plasticizers, is then used to attempt to obtain desired values. For example, U.S. Pat. Nos. 4,587,101; 4,752,115 and 5,043,286 disclose that unplasticized polymers offer relatively poor performance when used in gas sensing membranes. However, plasticized membranes are disadvantageous in that plasticizer can leach out, affecting oxygen permeability over time.

In addition, U.S. Pat. No. 4,476,870 discloses that oxygen sensing membranes having low oxygen permeable membranes are relatively insensitive. However, while adding more dye to a membrane can increase signal sensitivity, this can also reduce or alter oxygen permeability.

Thus, the combination of a particular polymeric material and fluorescent dye molecule, used to provide an oxygen sensing membrane, has generally been made in an ad hoc manner, and the sensitivity of a particular polymeric sensing membrane has only been found a posteriori. As a result, known polymeric sensing membranes can require relatively complex and expensive equipment, offer relatively poor sensitivity or both. This situation is the direct result of the lack of a known method which allows one to a priori predict the Stern-Volmer constant of a polymeric sensing membrane.

SUMMARY

Accordingly, it is an object of the present invention to provide a polymeric sensing membrane having a Stern-Volmer constant within a predetermined range of Stern-Volmer constants.

It is another object of the present invention to provide a method of preparing such a membrane.

It is yet another object of the present invention to provide a polymeric sensing apparatus which includes such a membrane.

It is a further object of the present invention to provide a polymeric sensing membrane which has a Stern-Volmer constant within a predetermined range of Stern-Volmer constants and which is comprised of readily available materials.

It is still a further object of the present invention to provide a method of making such a membrane.

Accordingly, in one embodiment of the present invention a polymeric sensing membrane is provided. The polymeric sensing membrane has a Stern-Volmer constant within a predetermined range of Stern-Volmer constants this range generally between about $0.002 (mmHg)^{-1}$ to $1.0 (mmHg)^{-1}$, e.g., those selected from the group consisting of a) from approximately $0.007 (mmHg)^{-1}$ to approximately $0.011 (mmHg)^{-1}$ b) from approximately $0.002 (mmHg)^{-1}$ to approximately $0.005 (mmHg)^{-1}$ and c) from approximately $0.2 (mmHg)^{-1}$ to approximately $1.0 (mmHg)^{-1}$. The polymeric sensing membrane comprises a fluorescent dye molecule which has a relaxation time. The dye molecule is capable of being collisionally quenched by the gas to which the polymeric sensing membrane is sensitive. The membrane further comprises a polymer which has a permeability within a range of permeabilities defined by a mathematical function of the predetermined range of Stern-Volmer constants for the polymeric membrane. The dye molecule is dispersed within the polymer.

Another embodiment of the present invention provides a polymeric sensing membrane which comprises a polymer and a florescent dye molecule dispersed within the polymer. The polymeric sensing membrane has a Stern-Volmer constant within a predetermined range of Stern-Volmer constants selected from the group consisting of a) from approximately $0.007 (mmHg)^{-1}$ to approximately $0.011 (mmHg)^{-1}$, b) from approximately $0.002 (mmHg)^{-1}$ to approximately $0.005 (mmHg)^{-1}$ and c) from approximately $0.2 (mmHg)^{-1}$ to approximately $1.0 (mmHg)^{-1}$. The polymer has a desired permeability and the fluorescent dye molecule is capable of emitting fluorescence. The fluorescent dye molecule has a relaxation time within a range of relaxation times defined by a mathematical function of the predetermined range of Stern-Volmer constants of the polymeric sensing membrane. The membrane is preferably unplasticized.

A further embodiment of the present invention provides a method of synthesizing a polymeric sensing membrane having a Stern-Volmer constant within a predetermined range of Stern-Volmer constants. This method comprises first selecting step which includes either (a) selecting a dye molecule having a relaxation time, wherein the dye molecule is capable of emitting fluorescence which can be collisionally quenched by the gas to which the polymeric sensing membrane is sensitive or (b) selecting a polymer having a permeability. The method further includes a second selecting step which includes either (c) selecting a polymer having a permeability within a range of permeabilities defined by a mathematical function of the predetermined range of Stern-Volmer constants of the polymeric membrane, wherein the first selecting step comprises step (a) and (d) selecting a fluorescent dye molecule having a relaxation time within a range of relaxation times, wherein the range of relaxation times is defined by a mathematical function of the predetermined range of Stern-Volmer constants of the polymeric membrane, wherein the dye molecule is capable of emitting fluorescence which can be collisionally quenched by the gas, and wherein the first selecting step comprises step (b). The method further includes the steps of admixing the fluorescent dye molecule with the polymer to form a mixture and forming the mixture into a polymeric sensing membrane.

Yet another embodiment of the present invention provides an apparatus for determining oxygen levels in blood. The apparatus includes means for utilizing a constant phase measurement to provide as a direct output a source modulation frequency proportional to a partial pressure of the oxygen in the blood. The apparatus includes a polymeric sensing membrane which comprises a polymer and fluorescent dye molecule dispersed within the polymer. The membrane has a Stern-Volmer constant within a predetermined range of Stern-Volmer constants. The fluorescent dye molecule is capable of emitting fluorescence which can be collisionally quenched by oxygen, and the polymer has a permeability. The relaxation time of the fluorescent dye molecule is defined by a mathematical function of the predetermined range of Stern-Volmer constants for the polymeric membrane, wherein the predetermined range of Stern-Volmer constants of the membrane is from approximately 0.007 $(mmHg)^{-1}$ to approximately 0.011 $(mmHg)^{-1}$.

Still a further embodiment of the present invention provides an apparatus for determining oxygen levels in blood. The apparatus includes a means for utilizing a constant phase measurement to provide as a direct output a source modulation frequency proportional to a partial pressure of oxygen in the blood. The apparatus includes a polymeric sensing membrane which comprises a polymer and fluorescent dye molecule dispersed therein. The membrane has a Stern-Volmer constant within a predetermined range of Stern-Volmer constants. The fluorescent dye molecule is capable of emitting fluorescence with a relaxation time wherein the fluorescence is capable of being collisionally quenched by oxygen. The polymer has a permeability within a range of permeabilities defined by a mathematical function of the predetermined range of Stern-Volmer constants of the polymeric sensing membrane. The predetermined range of Stern-Volmer constants is from approximately 0.007 $(mmHg)^{-1}$ to approximately 0.011 $(mmHg)^{-1}$.

It is a feature of the present invention to provide an empirical approach and/or a theoretical approach to predicting the Stern-Volmer constant of a polymeric sensing membrane. Such an approach allows one to prepare and utilize a gas sensing membrane having a Stern-Volmer constant within a predetermined range of Stern-Volmer constants. Furthermore, this approach allows polymeric materials and fluorescent dye molecules to be synthesized for use in specific polymeric sensing membranes.

It is another feature of the present invention to provide a method which allows one to calculate certain desired properties of a polymeric material or a fluorescent dye molecule for use in a particular polymeric sensing membrane which is to be employed in a particular gas sensing measurement.

In certain embodiments, an advantageous feature of the present invention includes providing a polymeric sensing membrane capable of being used in a measurement apparatus that utilizes a relatively inexpensive and convenient excitation source for the dye molecule dispersed within the polymeric sensing membrane. Such a relatively inexpensive and convenient excitation source could be, for example, a solid state light emitting diode (LED).

In some embodiments, it is an advantage of the present invention that relatively inexpensive or readily available electronic equipment may be used in conjunction with a polymeric sensing membrane to measure or monitor the partial pressure of certain gases. Such equipment may have a frequency response of less than 100 Khz. Furthermore, an LED light source may be used with this electronic equipment.

DETAILED DESCRIPTION OF THE INVENTION

Figure 1:
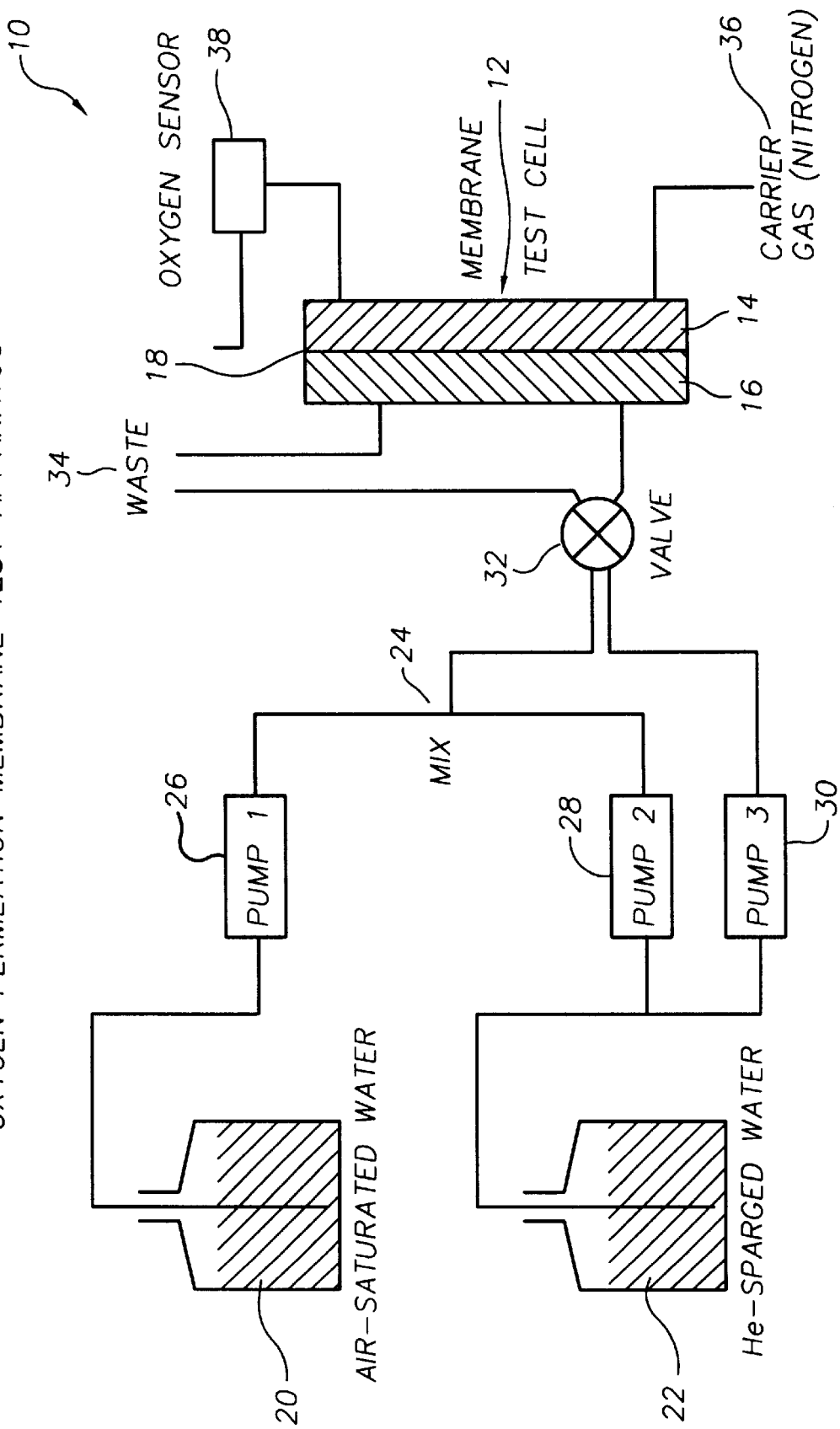
FIG. 1 is a schematic view of an apparatus capable of measuring a gas permeability of a polymeric sensing membrane in accordance with the present invention.

The present invention relates generally to polymeric sensing membranes which are capable of providing a predetermined level of sensitivity. Such polymeric sensing membranes have a Stern-Volmer constant within a predetermined range of Stern-Volmer constants. "Polymeric sensing membrane" herein denotes a membrane which is capable of sensing a gas, can be used to allow quantitive and qualitive detection of the gas and which comprises a polymeric material and at least one fluorescent dye molecule dispersed within the polymeric material. In certain embodiments, a polymeric sensing membrane may further include a substrate layer onto which the polymeric sensing material is disposed.

Polymeric sensing membranes in accordance with the present invention may have any thickness so long as the membrane has a Stern-Volmer constant within a predetermined range of Stern-Volmer constants as described herein. In certain embodiments, the polymeric sensing membrane preferably has a thickness of at most approximately 3 microns, more preferably at most approximately 2 microns and most preferably from approximately at most about 1.0 micron.

Providing a predetermined sensitivity to a polymeric sensing membrane involves undertaking a theoretical calculation of the Stern-Volmer constant for a membrane. According to the present invention, this theoretical calculation involves several mathematical steps. These mathematical steps are as follows:

First, equation (2) is substituted into equation (1), and the resulting equation is rearranged to yield $$k_{SV}=k_q \cdot \tau_O \cdot [O_2]/pO_2 \qquad (9)$$

However, it should be noted that the solubility of oxygen in a membrane is defined by Equation (10).

$$S_{O2}=[O_2]/pO_2 \qquad (10)$$

In addition, Equation (11) defines the quenching constant of a fluorescent dye molecule.

$$k_q=4\pi \cdot N_A \cdot p \cdot D_{O2} \qquad (11)$$

where $D_{O2}$ is the diffusion coefficient of oxygen, $N_A$ is Avogadro's number and p is a relative indication of the likelihood of an oxygen molecule colliding with an electronically excited fluorescent dye molecule. Substitution of equations (9) and (10) into equation (11) yields $$k_{SV} = 4\pi \cdot N_A \cdot p \cdot \tau_O \cdot [D_{O2} \cdot S_{O2}] \qquad (12)$$

However, the permeability of oxygen through a polymeric material is given by $$Perm_{O2} = D_{O2} \cdot S_{O2} \qquad (13)$$

So equation (13) may be rewritten as $$k_{SV} = 4\pi \cdot N_A \cdot p \cdot \tau_O \cdot Perm_{O2} \qquad (14)$$

This mathematical function relates the Stern-Volmer constant of a polymeric sensing membrane to the relaxation time of the fluorescent dye molecule and the oxygen permeability of the polymeric material in which the fluorescent dye molecule is dispersed.

Gas permeability is defined herein as the volume of gas (at standard temperature and pressure) that flows per unit time, multiplied by the thickness of the material, and divided by the area of the material and the pressure differential across the material in that area. Conversion to the Barrer unit standard:

$$(([cm^3] \times thickness\ [cm]) \times 10^{-10})/(area\ [cm^2] \times time\ [sec] \times P_{diff}[cm\ Hg])$$

is accomplished by standard conversion constants such as those disclosed in the *Polymer Handbook,* third edition, John Wiley & Sons, New York, N.Y., (1989).

Oxygen permeability values for polymeric materials used for polymeric sensing membranes may be measured according to the following method. A membrane of known thickness is mounted so as to be contacted on one side by flowing water having a predetermined partial pressure of oxygen while on the opposite side an equal membrane area is exposed to a flowing carrier gas without oxygen (i.e., nitrogen or helium). The flowing carrier gas is analyzed for oxygen content using a potentiometric palladium oxide sensor and the flux computed per unit time for a given area and thickness of membrane.

FIG. 1 shows an apparatus 10 for making oxygen permeation measurements using polymeric sensing membranes according to the present invention. A thermostatted flow cell 12 includes two matching stainless steel plates 14, 16 with identical serpentine paths. Plates 14, 16 can be bolted together to sandwich a polymeric sensing membrane 18. Vessels of air saturated water 20 and He-sparged water 22 may serve as reservoirs for either mixing test solutions in a mixing chamber 24 or wash purposes. The flow is controlled by HPLC pumps 26, 28, 30 and a valve 32 which diverts the flow either the flow cell 12 or to a waste container 34. Nitrogen is supplied to test cell 12 by a nitrogen gas source 36. After passing over membrane 18, the nitrogen gas flows into a palladium oxygen sensor 38 for potentiometric measurements.

Figure 2:
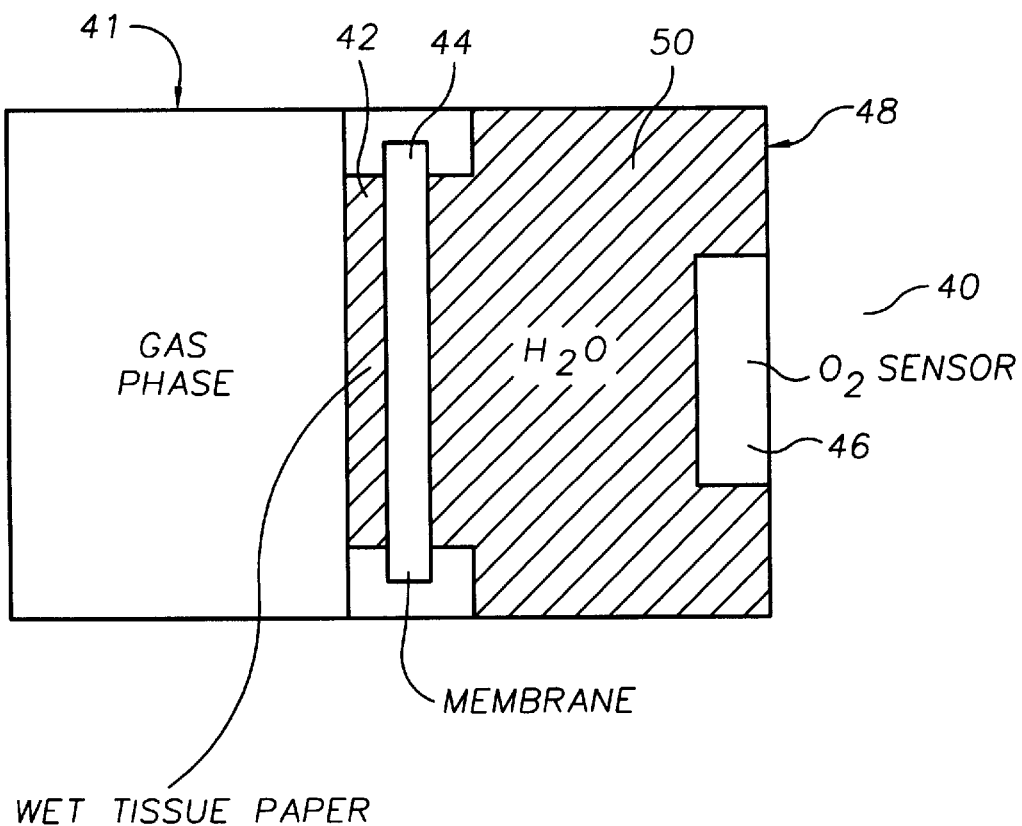
FIG. 2 is the cross sectional view of another apparatus capable of measuring a gas permeability of a polymeric sensing membrane in accordance with the present invention.

FIG. 2 depicts another apparatus 40 for measuring oxygen permeation using polymeric sensing membranes according to the present invention. In apparatus 40, a constant flow of gas containing a fixed concentration of oxygen passes through chamber 41 over a wetted tissue paper 42 on one side of the membrane 44. An oxygen sensor 46, such as a Clark electrode, monitors the rate of oxygen increase in a chamber 48 containing a stirred, fixed volume of water 50.

Another approach to measuring gas permeability is disclosed in *J. Polym. Sci.* 41, 1(1973). Other methods of measuring the permeability are known to those skilled in the art and are intended to be within the scope of the present invention.

A "fluorescent dye molecule" as used herein refers to a molecule which is capable of emitting fluorescence that can be quenched by the gas to be sensed by a polymeric sensing membrane. "Fluorescence" herein denotes the emission of radiation by a fluorescent dye molecule upon the electronic de-excitation of the molecule. The de-excitation of the fluorescent dye molecule may occur with or without a change in the electronic spin of the electron undergoing de-excitation.

If the ratio of fluorescent dye molecule to polymeric material in a polymeric sensing membrane is too high, the dye molecule may coalesce, resulting in a decrease in gas permeability through the membrane. Accordingly, the relative amount of the dye molecule dispersed within a polymeric sensing membrane should not be so high as to allow the dye molecule to aggragate and given rise to non-ideal behavior. Preferably, a polymeric sensing membrane comprises at most approximately 4% fluorescent dye molecule by weight, more preferably at most approximately 2% fluorescent dye molecule by weight and most preferably at most approximately 1% fluorescent dye molecule by weight.

Fluorescent dye molecules appropriate for use in the present invention are limited only in that they should have their fluorescence emission quenched by the gas to be sensed and in that they should be capable of being dispersed within a polymeric material. Such fluorescent dye molecules include, for example, those disclosed in U.S. Pat. No. 5,043,286. Other dyes which may be used in the present invention include, but are not limited to, ruthenium complexes such as disclosed in U.S. Pat. No. 5,030,420, *J.A.C.S.* 93, 3184 (1971) and *Anal. Chem.* 63, 337, (1991), porphyrin derivatives as disclosed in U.S. Pat. Nos. 4,810,655 and 5,043,286 as well as *Biosensors and Bioelectronics* 7, 199 (1991), and lanthinide complexes such as disclosed in U.S. Pat. Nos. 4,861,727 and 5,190,729. Other dyes which may be used in the present invention will be apparent to those skilled in the art and are intended to be within the scope of the present invention. It is to be noted that, according to the present invention, a particular fluorescent dye material may be synthesized for a particular use with a given polymeric material based on the desired Stern-Volmer constant of the polymeric sensing membrane.

A nonlimiting and exemplary list of fluorescent dye molecules which are appropriate for use in the present invention includes tetrabenzo-Pt-porphyrin, tetraphenyl-Pt-porphyrin, octaethyl-Pt-porphyrin keton, octaethyl-Pt-porphyrin, octaethyl-Pt-chlorin, tetraphenyl-Pt-chlorin, (4,7-diphenyl-1,1-phenanthroline)$_3$ Ru(II), ligand metal complexes of ruthenium (II), osmium (II), iridium (III), rhodium (III) and chromium (III) ions with 2,2-bipyridine, 1,10-phenanthroline, 4,7-diphenyl-(1,20-phenanthroline), 4,7-dimethyl-1, 10-phenanthroline, 4,7-disulfonated-diphenyl-1,10-phenanthroline, 5-bromo-1,10-phenanthroline, 5-chloro-1,10-phenanthroline, 2-2'bi-2-thiazoline, 2,2'-bithiazole, and other α-diimine ligands and porphyrin phthalocyanine complexes of $VO^{2+}$, $Cu^{2+}$, $Zn^{2+}$, $Pt^{2+}$ and $Pd^{2+}$ or dimeric Rh, Pt, or Ir complexes.

Selection of a particular fluorescent dye molecule typically depends, at least in part, upon certain photo-physical properties of the fluorescent dye molecule. A comparison of some of these properties is presented in Table I for several selected fluorescent dye molecules in solution. The quantum yields of these dye/solution systems were determined on a Perkin-Elmer MPF-66 Fluorescence Spectrometer, and the absorption measurements were performed on a Perkin Elmer Lambda 19 UVNIS/NIR Spectrometer. Luminescence lifetimes ($\tau_O$) of the fluorescent dye molecules in solution were measured using a model 199S Edinburgh Instruments Fluorescence Decay Time Spectrometer. In addition, by dispersing the dye molecules within polystyrene (available from Aldrich, Milwaukee, Wis. with an average molecular weight of 280,000), luminescence lifetimes for the dye molecules in a model polymeric sensing membrane could be obtained. These measurements were made using short excitation flashes with a Perkin Elmer LS-50 Spectrofluorimeter under flowing $N_2$ gas at room temperature. As shown in Table I, the luminescence lifetime for a fluorescent dye molecule is relatively independent of whether the dye molecule is measured in solution or dispersed within a polymeric material, so existing experimental data on fluorescent dye molecules in solution can often be used to at least approximate the fluorescence lifetime of the same dye molecule dispersed within a polymeric material. The present invention preferably employs a fluorescent dye molecule having a relaxation time of from approximately 1 microsecond to 45 microseconds, and from approximately 45 microseconds to approximately 120 microseconds.

It is possible that dispersing a dye molecule within a polymeric material may cause the fluorescence lifetime of the dye molecule to vary from ideal behavior. Such non-ideal behavior would be demonstrated by not being able to fit fluorescence lifetime data for fluorescent dye molecules in a polymer using a single exponential in a manner similar to the ideal solution case where a single dynamic quenching mechanism can be observed for appropriate dyes. Fitting curves for the fluorescence lifetimes of the porphyrin/polysterene membranes listed in Table I, using a single exponential, yielded correlation coefficients of 0.999. Thus, for practical purposes, one may assume the behavior of the tested porphyrins, dispered in a polymer, does not deviate substantially from an ideal solution case.

In many instances, it may be advantageous to use a fluorescent dye molecule that has a high quantum yield or that fluoresces a relatively high percentage of the radiation which the molecule absorbs. "Quantum yield" as used herein denotes the ratio between the number of photons which are absorbed by a fluorescent dye molecule to cause an electron within the dye molecule to undergo a transition from the ground state to an excited state and the number of photons which are emitted by the dye molecule upon the return of the electron to the ground state from the excited state. According to the present invention, a fluorescent dye molecule preferably has a quantum yield of at least approximately 0.1, more preferably at least approximately 0.25 and most preferably at least approximately 0.5.

Typically, a fluorescent dye molecule should absorb a relatively high amount of the radiation to which the dye molecule is exposed. This property may be measured by the extinction coefficient. The term "extinction coefficient" as used herein refers to the absorbance of light by a one molar solution having a pathlength of 1 cm. According to the present invention, a fluorescent dye molecule preferably has an extinction coefficient of at least approximately 20,000 L/mol-cm, more preferably at least approximately 50,000 L/mol-cm and most preferably at least approximately 75,000 L/mol-cm.

As known to those skilled in the art, neither the quantum yield nor the extinction coefficient alone are true measures of the efficiency with which a fluorescent dye molecule converts incident radiation to fluorescence. However, the product of the quantum yield and the extinction coefficient can be used as a guide in determining a dye molecule's efficiency in converting incident radiation to fluorescence. Using this quantity as an indicator of efficiency, Table I demonstrates that the ruthenium diphenylphenanthroline complex (high quantum yield, low extinction coefficient) and the octaethyl porphyrin molecule (medium quantum yield, medium extinction coefficient) are relatively efficient in converting incident radiation to fluorescence. Furthermore, it should be noted that the octaethyl porphyrin has a relatively long decay time which may be particularly useful with sensor systems having lower frequency response electronics instrumentation.

To decrease the cost of using polymeric sensing membranes, it is often desirable to use a fluorescent dye molecule for which excitation, detection of fluorescence and processing of signal information can be carried out using relatively simple electronic equipment. Readily available excitation sources include flashlamps, tungsten halogen lamps, light emitting diodes (LEDs), lasers and laser diodes. All these excitation sources may be used in accordance with the present invention, but LEDs are often preferable because they provide an inexpensive, low power consumption source of radiation. However, it should be noted that LEDs output relatively narrow bands of radiation. Therefore, for a given fluorescent dye molecule/LED combination, the absorption wavelength of the dye molecule should approximately match the peak output wavelength of the LED. Thus, the selection criteria provided by the present invention are especially important for matching a polymer with a dye chosen to match the peak output wavelength of an excitation source, such as an LED.

To optimize the sensitivity of a given polymeric sensing membrane, the emission spectrum of the fluorescent dye molecule dispersed within the membrane should be compatable with the peak sensitivity of a chosen detector. While shortwave emission (approximately 200 nm to approximately 600 nm) output is detectable with most photomultiplier tubes, lower cost solid state detection circuitry is often advantageous for detecting emission at comparatively longer wavelengths of approximately 600 nm to approximately 1000 nm. Thus, it is often preferable to use photodiodes to detect porphyrin dyes with emission peaks in a range of approximately 650 nm to approximately 780 nm.

The response time requirement of the electronic instrumentation used to measure the decay time of a polymeric sensing membrane depends upon the fluorescence lifetime of the fluorescent dye molecule dispersed within the membrane. Longer unquenched ($\tau_O$) and quenched ($\tau$) fluorescence lifetimes lower the frequency response necessary for detection and processing. This generally allows slower, more readily available and less expensive electronic equipment to be used when performing a measurement using a polymeric sensing membrane. For example, when used in a polymeric sensing membrane, the ruthenium diphenylphenathroline dye listed in Table I ($\tau_O$=11.4 $\mu$secs) would require instrumentation operating at a minimum frequency range of approximately 27 kHz to approximately 270 kHz. In contrast, a polymeric sensing membrane including the octaethyl-Pt-porphyrin listed in Table I ($\tau_O$=85 $\mu$secs) as the fluorescent dye molecule could operate in a minimum frequency range from approximately 2 kHz to approximately 20 kHz. The present invention provides a systematic solution of a polymeric membrane compatible with a dye chosen to match a single detection system. The present invention is capable of providing the systematic selection of a dye molecule, polymeric material or combination thereof that is compatible with a detection system. Preferably, such a detection system is simple and comprised of readily available components.

TABLE I

DYE PHOTO-PHYSICAL PROPERTIES

| DYE | Ru(II) | OEC | OEP | OEPK | TBP |
|---|---|---|---|---|---|
| Excitation ($\lambda_{nm}$) | $(460)^\#$ | 596 | 535 | $(592)^*$ | 594 |
| $\epsilon$(L mol$^{-1}$ cm$^{-1}$) | $(30,000)^\#$ | 69,000 | 55,400 | $(55,100)^*$ | 20,900 |
| Emission ($\lambda_{nm}$) | $(600)^\#$ | 780 | 650 | $(759)^*$ | 756 |
| Quantum Yield $\phi_o$ | $(0.5)^\#$ | 0.05 | 0.38 | $(0.12)^*$ | 0.2 |
| $\phi_o/\phi_{air}$ | — | 70 | 400 | — | 50 |
| $\tau_o$ ($\mu$secs) in solvent @ 23° C. | $(5.9)^\#$ | 45 | 100 | — | 40 |
| $\tau_o$ ($\mu$secs) in polystyrene | $(11.4)^\%$ | 40 | 85 | 66 | 63 |
| $\epsilon \cdot \phi_o/1000$ | 15.0 | 3.5 | 21.0 | 6.6 | 4.2 |
| LED | Blue | Yellow | Green | Yellow | Yellow |
| Emission ($\lambda_{nm}$) | 550 | 580 | 555 | 580 | 580 |

Abbreviations:
Ru(II): (4,7 diphenyl-1,10-phenanthroline)$_3$Ruthenium(II);
OEC: octaethyl-Pt-chlorin;
OEP: octaethyl-Pt-porphyrin;
OEPK: octaethyl-Pt-porphyrin ketone;
TBP: tetrabenzo-Pt-porphyrin
Values in ( ) taken from published Literature.
Demas U.S. Pat. No. 5,030,420
%Draxler et. al, (1995) J Phys. Chem. 99:3162–3167.
*Joanneum Institute product literature A "polymeric material" as used herein refers to a polymerization product incorporating repeating chemical units. Polymeric materials appropriate for use in the present invention should: 1.) be capable of having a fluorescent dye molecule dispersed therein; 2.) be an optically transparent material; and 3.) have a permeability towards a gas to be sensed that is greater than zero.

Polymeric materials may be arranged either as homopolymers or copolymers. "Homopolymers" as used herein refers to polymeric materials which include one repeating chemical unit. By "copolymers" it is herein meant to refer to a polymeric material including more than one repeating chemical unit. Homopolymers and copolymers may include alternating polymers, random polymers, statistical polymers, block polymers, graft polymers, linear polymers, branched polymers (including star polymers, comb polymers, ladder polymers and semi-ladder polymers) and network polymers (i.e., cross-linked polymers). While a list of certain arrangements of polymeric materials have been disclosed herein, it is to be appreciated that polymeric materials appropriate for use in the present invention may be arranged in any manner so long as such polymeric materials have the desired properties disclosed herein.

Typically, polymeric materials useful in the present invention are comprised of starting materials that include at least one of the following organic polymers: polystyrenes, polyalkanes, polymethacrylates, polynitriles, polyvinyls, polydienes, polyesters, polycarbonates, polysiloxanes, polyamides, polyacetates, polyimides, polyurethanes and derivatives thereof. Certain polymeric materials appropriate for use in the present invention and methods of making such polymeric materials are disclosed in U.S. Pat. No. 5,387,329. A list of polymeric materials appropriate for use in the present invention includes, but is not limited to, plexiglass, polyvinyl chloride (PVC), polystyrene, polycarbonate, latex, fluorinated polymers, such as Teflon®, polyvinylidene fluoride, poly(tetrafluoroethylene propylene), cation and anion exchange resins, polyurethane and polyethylene. As known to those skilled in the art, some of these polymeric materials, such as polystyrene, have comparatively high gas permeabilities while other of these polymeric materials, such as acrylonitrile, have relatively low gas permeabilities. The present invention preferably uses a polymer having a permeability of from approximately 0.47 seconds to approximately 2.05 Barrers, and from approximately 2.05 Barrers to approximately 611 Barrers. In certain embodiments, a polymeric sensing membrane may advantageously include a high gas permeability polymeric material and a low gas permeability polymeric material. While certain polymeric materials and combinations thereof have been disclosed herein, other polymeric materials appropriate for use in the present invention, combinations thereof and methods of making the same will be apparent to those skilled in the art and are intended to be within the scope of the present invention.

Often, polymeric sensing membranes include external plasticizers. As discussed above, the prior art includes references which suggest that the use of plasticizers may be advantageous. However, over time these plasticizers can leach out of the membrane producing changes the composition of the membrane. This can result in early or unwanted deterioration of the membrane's properties. Furthermore, a change in the composition of the polymeric sensing membrane can result in irreproducibility in measurements made with the membrane, that is, early failure. Thus, the present invention utilizes polymeric sensing membranes that have low plasticizer content, preferably membranes that are unplasticized. The terms "unplasticized" or "low plasticizer content" as used herein with respect to a polymeric material or products containing a polymeric material (e.g., polymeric sensing membranes) refers to a leachable plasticizer. According to the present invention, a polymeric sensing membrane will have substantially no plasticizer leach therefrom when the membrane is immersed in a liquid test sample at 37° C. for preferably at least about 1 hour, more preferably at least about 8 hours and most preferably at least about 72 hours. Preferably, the polymeric material or products containing the polymeric material include at most approximately 25% external plasticizer by weight, more preferably at most approximately 18% external plasticizer by weight, still more preferably at most approximately 10% and most preferably at most approximately 5% external plasticizer by weight. In a particularly preferred embodiment of the present invention, a polymeric sensing membrane includes approximately 0% external plasticizer.

In certain embodiments of the present invention, it may be desirable that a polymeric sensing membrane have a particular durability. For example, for certain implementations the membrane may be in contact with or compressed against a gasket, and such contact or compression should not negatively effect the ability of the membrane to be used for sensing measurements. Thus, the contact or compression should not cause the membrane to tear. Hence, in some embodiments, the polymeric sensing membrane preferably includes a polymeric material that has a Shore A hardness of at least approximately 20, more preferably at least approximately 50, and most preferably at least approximately 70 as measured according to the well-known ASTM standard procedures.

In certain embodiments of the present invention, the water uptake characteristics of a polymeric material may be important. For example, in many cases if a polymeric sensing membrane is exposed to water or water vapor and becomes hydrated, the permeability of the membrane can change. In addition, hydration of the membrane can cause the fluorescence lifetime of the dye molecule dispersed within the membrane to change through dipole effects on the ground and excited state transitions. Therefore, for embodiments in which a polymeric sensing membrane is exposed to water or water vapor, polymeric materials should have water uptake characteristics that allow the permeability and fluorescence lifetime to be unaffected by hydration of the membrane vapor over the course of an experiment. For such embodiments, the polymeric material should either have relatively low or slow water uptake so that the membrane does not become substantially hydrated over the course of an experiment or relatively high or fast water uptake so that the membrane is substantially hydrated before measurements occur. Examples of polymeric materials having relatively low or slow water uptakes are polystyrenes, and examples of polymeric materials having relatively high or fast water uptakes are acrylamides.

The flexibility of a polymeric sensing membrane depends upon the flexibility of the polymeric material included in the membrane. For some uses, it may be desirable for a polymeric sensing membrane to be relatively flexible. Such flexibility would allow the membrane to conform to certain nonuniformities between mating surfaces. In addition, a flexible membrane may preclude the use of a sealing gasket in some sensor chamber constructions. Furthermore, a flexible membrane is usually less likely to become delaminated from a substrate layer.

Typically, the flexibility of a polymeric sensing membrane is related to the polymeric material's glass transition temperature ($T_g$). It should be noted that, since many of the physical properties of polymeric materials, including permeability, change at or near the glass transition temperature, polymer sensing membranes appropriate for use in the present invention should not have a glass transition temperature near the intended temperature of use. For example, a membrane intended for use in the measurement of the oxygen content in whole blood samples at 37° C. should not have a glass transition temperature near 37° C. However, the membrane would preferably have a glass transition temperature elsewhere between approximately −40° C. and approximately 110° C. Likewise, a polymeric sensing membrane intended for use in cold fermentations between 5–7° C. should not have a glass transition temperature in this range.

Polymeric sensing membranes according to the present invention may also include a substrate onto which the polymeric material having a fluorescent dye material dispersed therein is placed. Such substrates should comprise an optically clear material. "Optically clear material" herein denotes a material which preferably transmits approximately at least approximately 95% of the electromagnetic radiation used to stimulate the electronic excitation of the fluorescent dye material and the fluorescence emission of the fluorescent dye material, more preferably at least approximately 98%, and most preferably at least approximately 99% as measured by the standard transmission mode.

Substrates appropriate for use in the present invention preferably have a permeability of at most approximately 0.05 Barrers, more preferably at most 0.005 Barrers, and most preferably at most approximately 0.0005 Barrers as measured by the methods disclosed in J. Membrane Sci. 9, 53 (1981). An exemplary and nonlimiting list of substrates includes mylars, polyethyleneteraphthalates (PET's), saran and glass. While certain materials appropriate for use in substrates in the present invention have been disclosed herein, it is to be appreciated that other materials which can be used in accordance with the present invention will be apparent to those of ordinary skill in the art and intended to be within the scope of the present invention.

Figure 3:
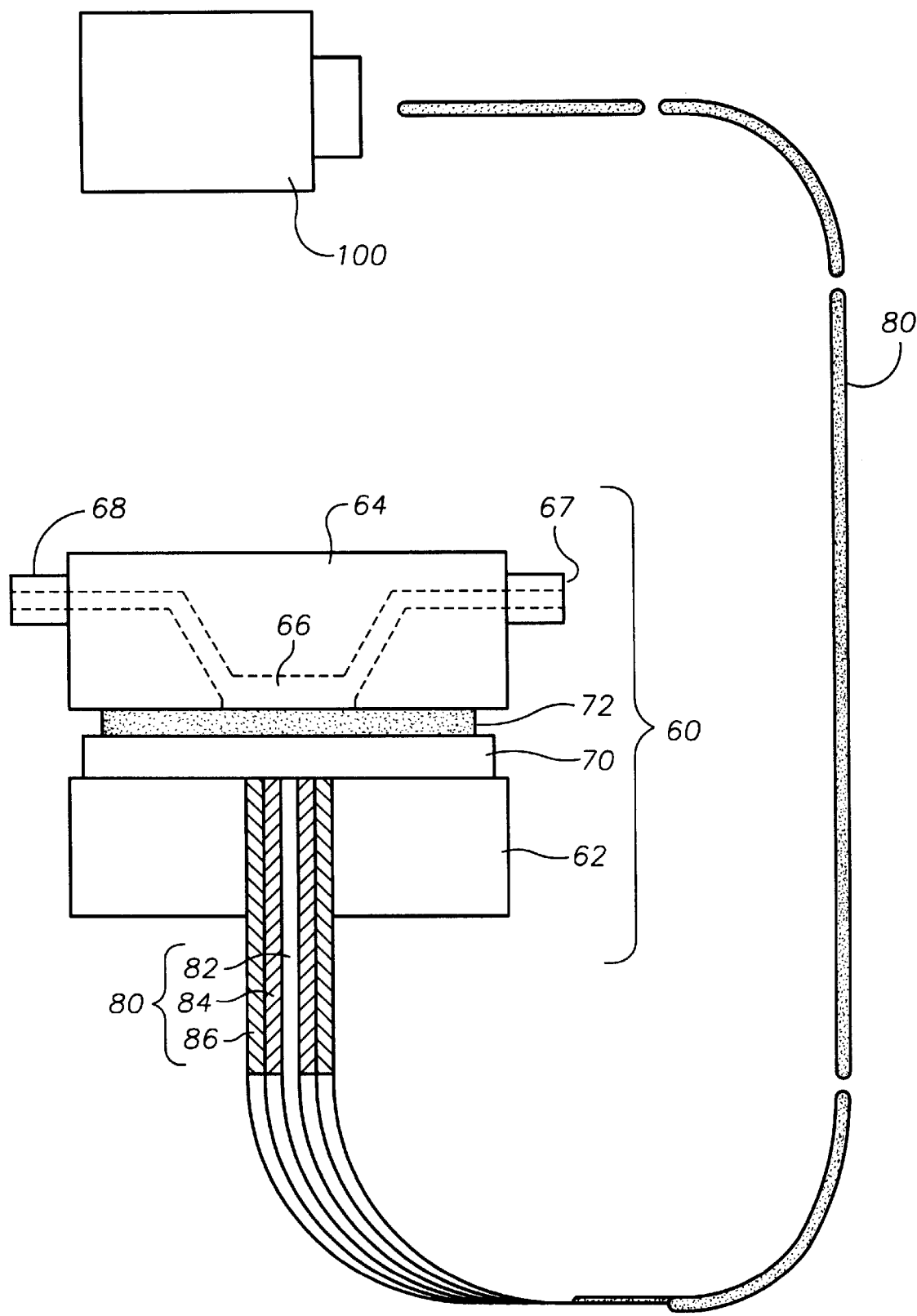
FIG. 3 is a schematic diagram of a sample chamber and sensor illumination device used in measurement of polymeric sensing membranes in accordance with an embodiment of the present invention.

The present invention, according to another aspect, provides a sample measurement apparatus constructed and arranged to quickly and reproducibly determine the existence and/or amount of a gas in a sample. As shown in FIG. 3, polymeric sensing membrane 72 is cast onto a substrate 70 and placed in the sampling chamber 60. The radiation impinging upon membrane 72 and emitted from membrane 72 is guided to source/detection system 100 by a fiber optic cable 80. Cable 80 includes a core 82, cladding 84 and sheath 86 where the core 82 and cladding 84 may be constructed from either glass or plastic polymer materials. Cable 80 is imbedded into base 62 which preferably has a low permeability and a polished smooth flat surface for contact with substrate 70. Base 62 may comprise stainless steel or another hard, thermally conductive material which is capable of assisting in controlling the temperature of membrane 72. Source radiation from cable 80 passes through substrate 70 and excites the fluorescent dye molecule dispersed within membrane 72. Pressed flat against membrane 72 is a hard flat thermally conducting material plate 64 which has either a cast or milled sample chamber 66 into which samples may be entered and subsequently removed through the entrance 67 and exit 68 ports. The signal from membrane 72 is then transmitted by cable 80 and returned to source/detector system 100.

Figure 4:
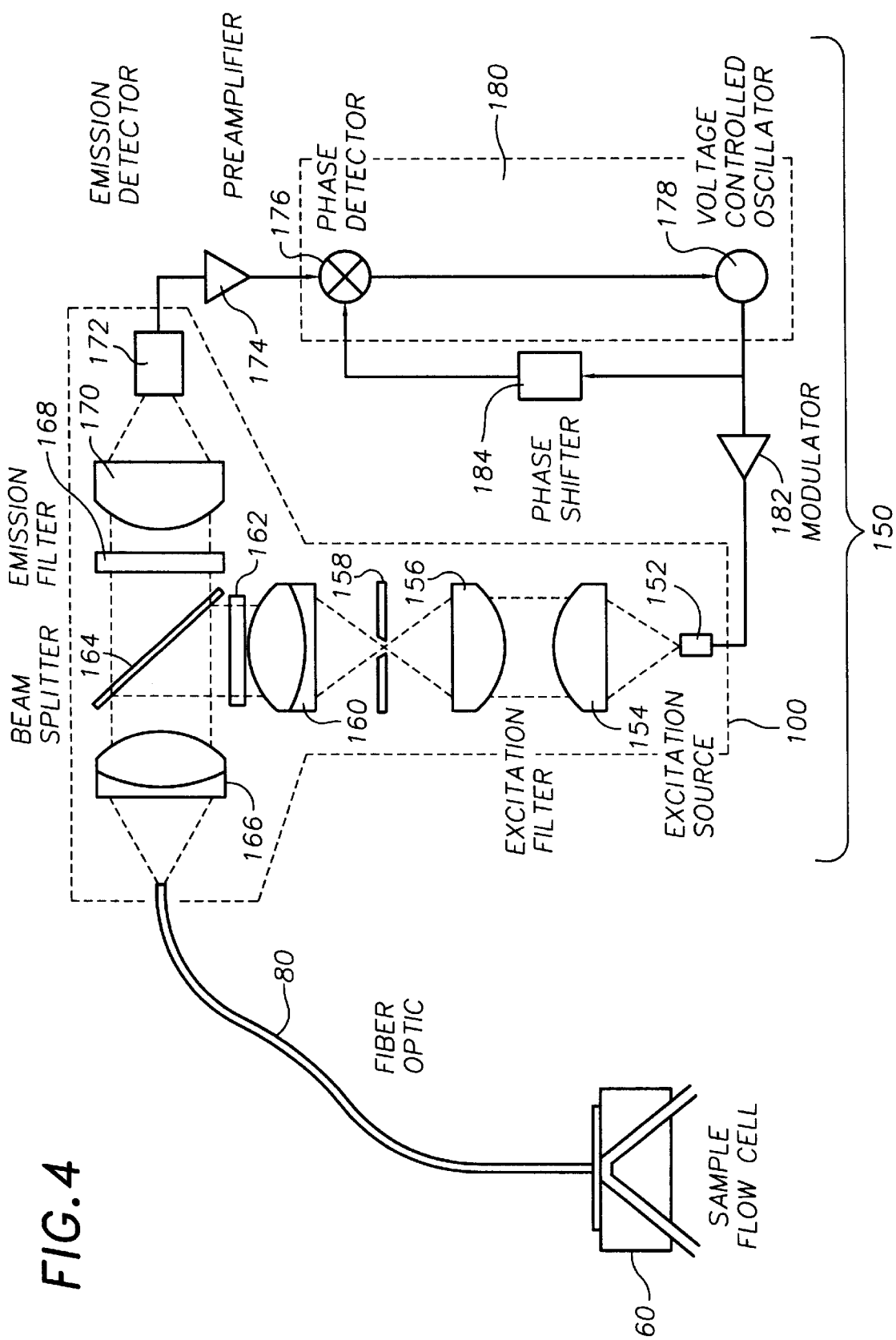
FIG. 4 is a schematic diagram of an apparatus capable of measuring the fluorescence amplitude or frequency response of polymeric sensing membranes in accordance with an embodiment of the present invention.

According to one embodiment, a detection apparatus is constructed and arranged to determine the presence of a gas by measuring fluorescence quenching of a dye by the gas. FIG. 4 shows an optical detection apparatus 150 for measuring gas levels using polymeric sensing membranes according to the present invention. Apparatus 150 can be implemented in measuring the fluorescence emission amplitude of a fluorescent dye molecule dispersed within a polymeric sensing membrane. In addition, the apparatus may be utilized in the constant phase detection method with polymeric sensing membranes. The apparatus includes an excitation source 152, such as a yellow LED (HAY5066X from Stanley Electric Co.). The light emitted by source 152 is collected and focused by a lens system containing a 12 mm focal length aspheric condenser lens 154, a second identical aspheric 156 for refocusing the light on a 400 $\mu$ pinhole 158 and a 22 mm focal length achromat 160 for collecting pinhole imaged light. The light passes through an interference filter 162, such as a bandpass interference filter (obtained from Omega Optical, Battleboro, Vt.). Filter 162 is preferably centered at the peak emission wavelength of the excitation source. In addition, filter 162 should have a comparatively narrow bandwith. For example, when excitation source 152 is a yellow LED, filter 162 is centered at 590 nm with a bandwidth of 50 nm. Alternatively, when excitation source 152 is a green LED (a suitable green LED can be HBG 5066X from Stanley Electric Co.), filter 162 may be centered at 540 nm. After passing through filter 162, the light reflects off a mirror 164. Mirror 164 should be capable of cutting off certain undesired wavelengths of light. For example, when excitation source 152 is a yellow LED, mirror 164 may be a 645 nm cutoff dichroic mirror (a suitable mirror may be purchased from Omega Optical, Brattleboro, Vt). If source 152 is a green LED, mirror 164 may be a 585 nm cutoff dichroic mirror (such a mirror may be 585 DLRP from Omega Optical, Brattleboro, Vt). Subsequent to its reflection off mirror 164, the light passes through an achromat lens 166 and is focused onto a glass fiber optic core 82 which is 400 μ in diameter. Achromat 166 may advantageously have a particular focal length which depends upon excitation source 152. For example, when using a yellow LED, achromat 166 may be a 22 mm focal length achromat (such as, for example, 01 LAO014 from Melles Griot). The distal sensing end 81 of fiber cable 80 is in physical contact at an angle of 90° with a glass or plastic substrate 70 that supports polymeric sensing membrane 72. The substrate and membrane are preferably in a stainless steel flow chamber 60. Reflected and emitted light from membrane 72 is collected by fiber cable 80 and passed through mirror 164. The light then passes through interference filter 168. The type of filter used for interference filter 168 may depend upon the fluorescent dye molecule and/or the excitation source. For example, if excitation source 152 comprises a yellow LED and the dye is tetrabenzyl-Pt-porphyrin, filter 168 may be a 775 nm interference filter (Omega Optical) having a passband of 50 nm. Alternatively, when the dye is octaethyl-Pt-porphyrin and the source 152 is a green LED, filter 168 may be centered at 645 nm. The filtered fluorescent emission light is subsequently focused by lens 170 onto an emission detector 172 (such as a JML meniscus lens CMN 11200/100 and a Hamamatsu R-3896 photomultiplier tube). While a particular arrangement of detection apparatus 100 has been disclosed herein, other equivalent detection apparatuses are known to those skilled in the art and are intended to be within the scope of the present invention. Furthermore, replacement of individual components with equivalent components, such as dichroic mirror 164 with a simple beam splitter, or photomultiplier detector 172 with a photodiode, are within the scope of the present invention.

The output current of emission detector 172 is amplified with a preamplifier 174, such as a Stanford Research SR570 current preamplifier. After passing through preamplifier 174, the signal is fed into a phase detector 176, such as that found in a Stanford Research SR530 Lockin Amplifier 180. Phase detector 176 compares its input signal to the phase of the signal from the SR530 oscillator 178 used to modulate the excitation source through a driver or modulator circuit 182; an offset signal is added by the phase shifter 184, such that the output of the phase detector 176 is proportional to the deviation of the emission signal from the desired phase lag of approximately 45 degrees. Since it is known from the nature of the sensor response that an increase in modulation frequency will result in a increased phase lag, this phase error signal can be used to control the frequency of the modulation signal source 178, completing the feedback loop.

One example of the response of apparatus 150 to changes in the partial pressure of oxygen is as follows. Initially, a constant partial pressure of oxygen is in contact with membrane 72, and the signal at the phase detector 176 is 45 degrees out of phase with the output signal of excitation source 152. If the oxygen partial pressure increases, the relaxation time of the sensor emission decreases, causing the phase lag to decrease. This results in the production of an error signal by the phase detector 176. The signal from the phase detector will cause the modulation signal source 178 to increase its frequency to a level that produces a 45 degree phase shift, restoring the loop to equilibrium. If the oxygen partial pressure at the sensor decreases, the relaxation time increases and an inverse chain of events ensues. It should be noted that, if the response time of the feedback loop is significantly faster than the response time of the sensor then the loop response is invisible and the frequency of the modulation signal source 178 follows equation (8) (i.e., the signal is directly proportional to the oxygen partial pressure at the sensor). When apparatus 150 is used in amplitude mode, a low frequency signal, such as 87 Hz from the SR530 Lockin oscillator 178, can drive the LED current supply at a constant frequency. In addition, the amplifier can be locked onto the in phase signal component to the phase detector 176.

Figure 5A:
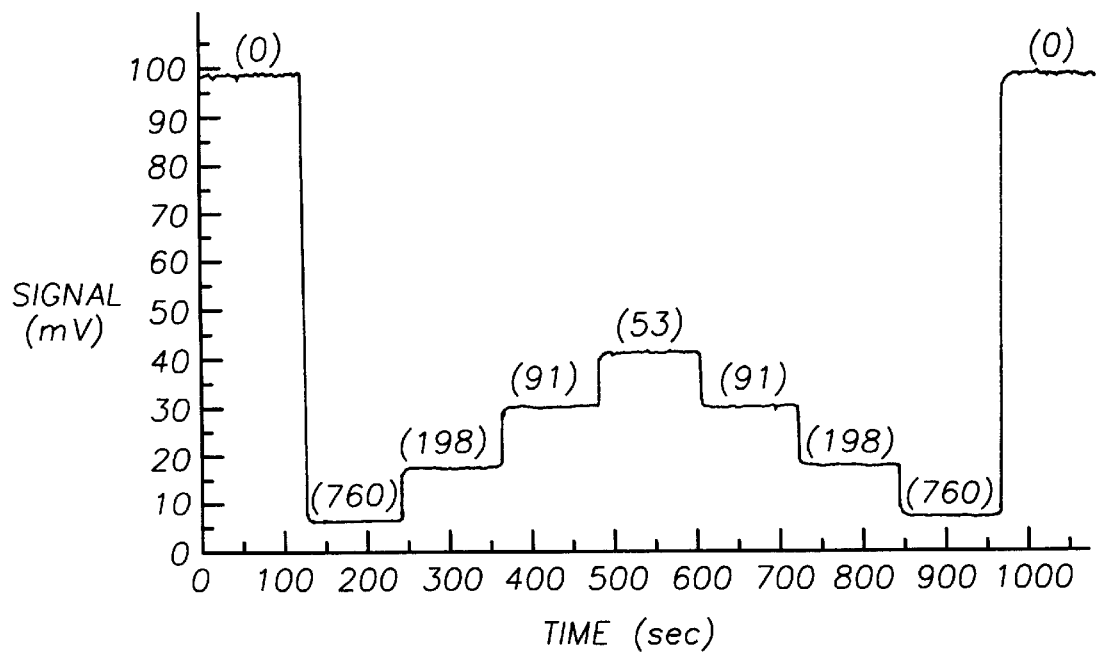
FIGS. 5A and 5B are plots of the fluorescence amplitude and frequency response, respectively, for a polymeric sensing membrane in accordance with the present invention.
Figure 5B:
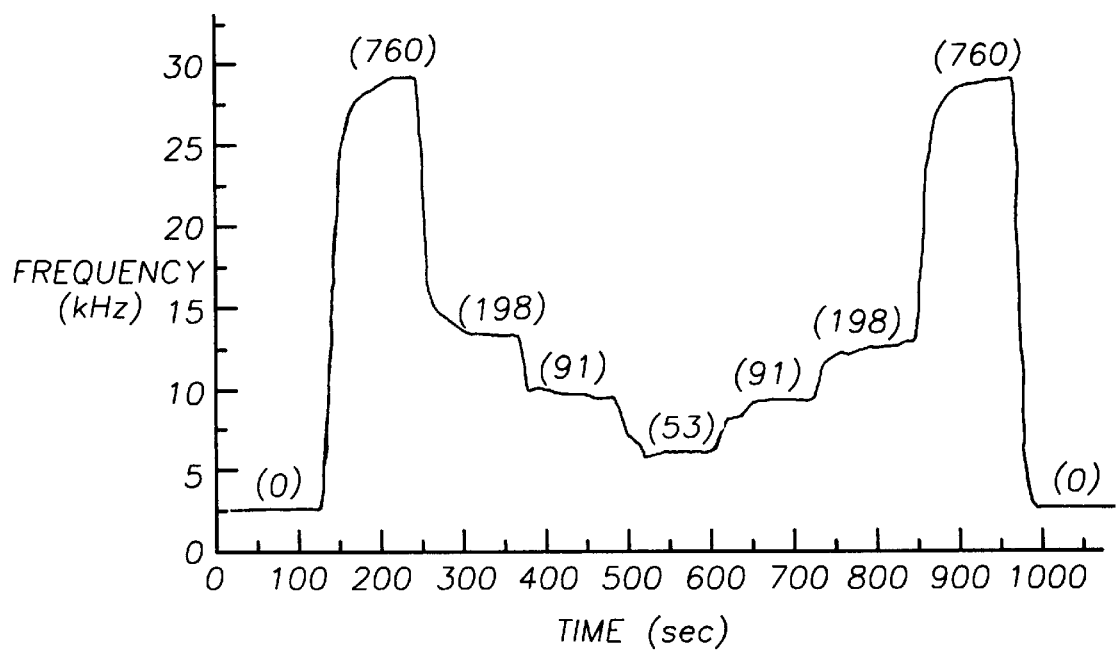

FIG. 5A depicts a typical Stern-Volmer emission quenching response, in terms of the measured signal in millivolts, for changes in the partial pressure (values given in mmHg in parenthesis) of oxygen in a gas stream flowing over a polymeric sensing membrane. The membrane comprised a tetrabenzyl-Pt-porphyrin dye and polystyrene, and the excitation source was a yellow light sinusoidally modulated at a constant frequency of 87 Hz. FIG. 5B shows the corresponding changes in the signal frequency for the same changes in the partial pressure of oxygen in a polystyrene membrane, when the LED was modulated at a frequency required to maintain a 450 phase shift in the fluorescence emission signal using the feedback loop described in FIG. 4.

Figure 6A:
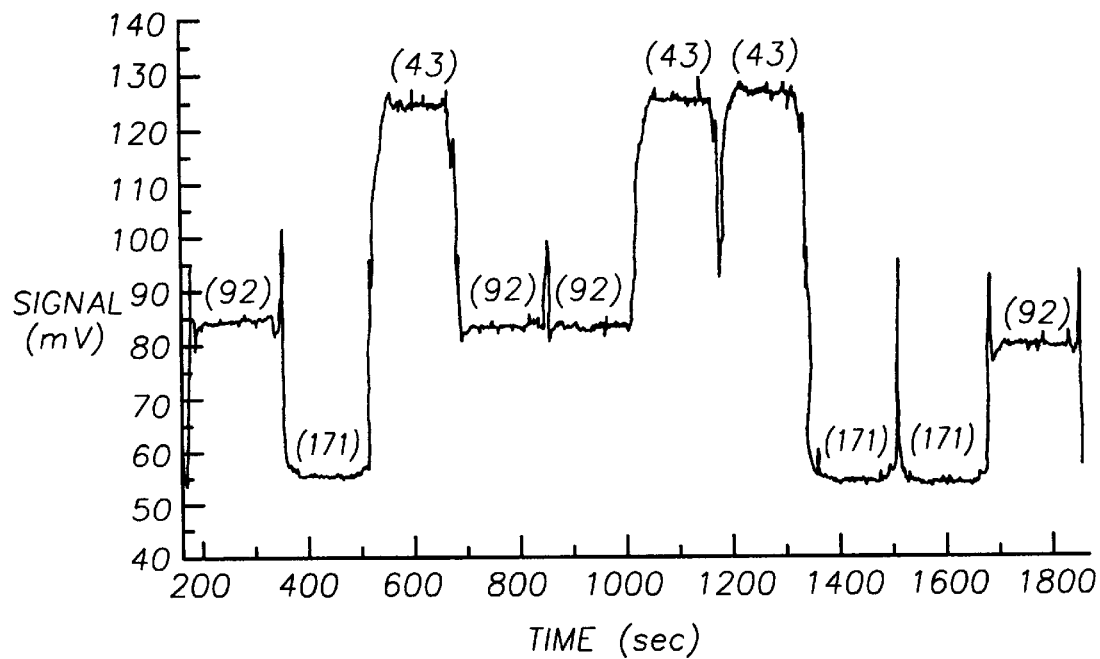
FIGS. 6A and 6B are plots of fluorescence amplitude and frequency response, respectively, to varying partial pressures of dissolved oxygen levels for a polymeric sensing membrane in accordance with the present invention.
Figure 6B:
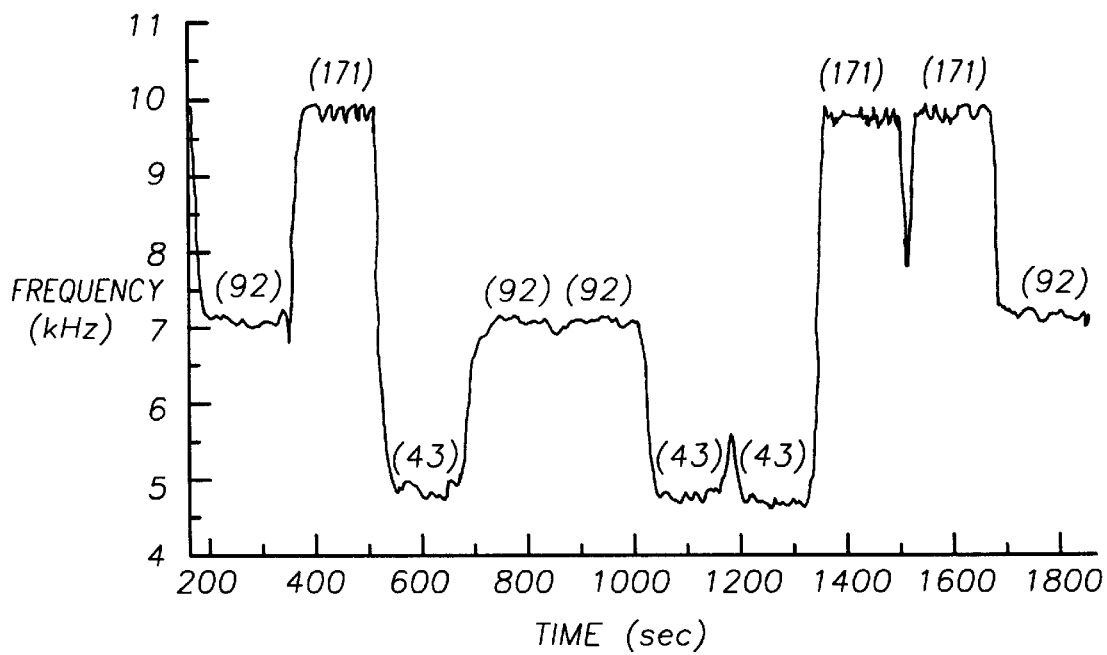

FIGS. 6A and 6B show similar response plots for changes in the partial pressure of oxygen, measured in similar units to FIGS. 5A and 5B, in tonometered aqueous buffers. The membrane comprised an octaethyl-Pt-porphyrin dye dispersed in polystyrene. FIG. 6A shows the fluorescence amplitude as a function of oxygen partial pressure changes with time, and FIG. 6B displays the frequency response to changes in the partial pressure of oxygen with time. It is possible to construct a Stern-Volmer curve from the fluorescent amplitude response to varying oxygen levels. By regression analysis of the slope, according to equation (2), the Stern Volmer constant ($k_{SV}$) may be determined. Likewise, if the frequency response is plotted for varying oxygen levels, the intercept ($\frac{1}{2}\pi\tau_O$) gives $f_O$ and the slope is measure of $t_O \cdot k_{SV}$, according to Equation (8 pk ).

According to the present invention, any method of preparing a polymeric sensing material having a predetermined range of Stern-Volmer constants may be used. In certain embodiments, it may be advantageous to dissolve the fluorescent dye molecule and the polymeric material in a solvent. For such embodiments, the solvent should be capable of dissolving the fluorescent dye molecule and the polymeric material without dissolving any substrate material which may be used. Such solvents include, for example, tetrahydrofuran (THF), chloroform and toluene. While certain solvents appropriate for use in the present invention have been disclosed herein, other solvents which may be used in accordance with the present invention will be apparent to those of ordinary skill in the art and are intended to be within the scope of the present invention.

To maximize the sensitivity of a polymeric sensing membrane, the measurement should be made under conditions where the fluorescence of the dye molecule changes by a comparatively large amount as the partial pressure of oxygen is changed (i.e., the signal should not be buried in the noise at the flat end of a Stern-Volmer quenching response curve). Therefore, a gas content measurement should be performed under conditions where the fluorescence signal of the dye molecule is half quenched at the mid range point of the desired dynamic range (MRP). "The mid range point of the desired dynamic range" is herein meant to refer to the midpoint of the range of gas pressure which is useful for a particular gas sensitivity measurement. For example, the in vitro measurement of the amount of oxygen in blood may have a dynamic range of from approximately 40 mmHg $pO_2$ to approximately 200 mmHg $pO_2$. Thus, the MRP would be 120 mmHg $pO_2$. Alternatively, a nearly anaerobic measurement of oxygen may occur in an oxygen pressure range of from approximately 0 mmHg $pO_2$ to approximately 10 mmHg $pO_2$. For this case, the MRP would be 5 mmHg $pO_2$. In addition, a high oxygen pressure measurement can occur in a range of oxygen pressure up to 800 mmHg $pO_2$. Therefore, the MRP would be 400 mmHg $pO_2$.

Using equation (2) and an oxygen partial pressure corresponding to the desired MRP to calculate the $k_{SV}$ required for optimized sensitivity of a polymeric sensing membrane yields $$F_O/F=2=1+k_{SV}\cdot(MRP)$$

or $$k_{SV}=1(MRP) \quad (15)$$

From equations (14) and (15) it is possible to compute either the Stern-Volmer constant ($k_{SV}$), the fluorescence lifetime ($\tau_O$) or the membrane permeability (Perm$_{O2}$) given any two of the other parameters assuming p is relatively constant between the dye and polymer systems under consideration. The useful range of Stern Volmer constants often spans three log orders, and the permeabilities of polymeric materials can vary over six log orders. Therefore, it is often convenient to rewrite equation (14) in a logarithmic form as $$log(k_{SV}/\tau_O)=log(4\pi\cdot N_A\cdot p)+log(Perm_{O2}) \quad (16)$$

where log ($4\pi\cdot N_A\cdot p$) may be determined to be a constant.

Figure 7:
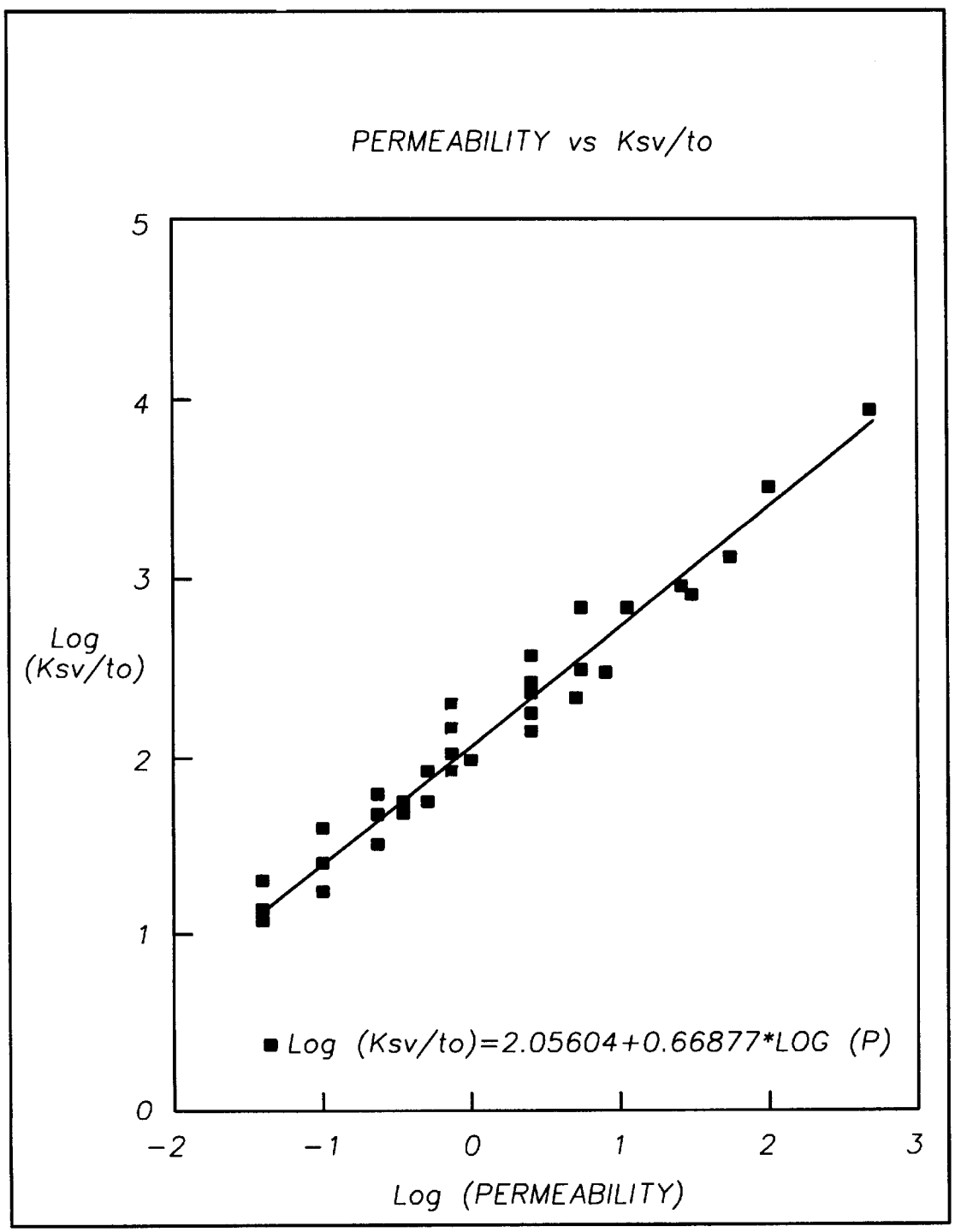
FIG. 7 is a plot of log $(k_{SV}/\tau_O)$ verses log (Permeability $O_2$) for several oxygen sensing membranes in accordance with the present invention.

A plot of log ($k_{SV}/\tau_O$) verses log (Perm$_{O2}$) is shown in FIG. 7 for several oxygen sensing polymeric membranes according to the present invention. The corresponding data for FIG. 7 is listed in Table II along with the calculated values for log ($k_{SV}/\tau_O$) derived from the slope and intercept values obtained from a linear curve fit. The polymer abbreviations shown in Table II are meant to uniquely identify the individual polymer materials having the measured properties set forth in Table II.

TABLE II

| POLYMER/DYE | PERM(P) | LOG(P) | $K_{sv}$ | LOG($K_{sv}$) | LOG($K_{sv}/t_0$) | Calc |
|---|---|---|---|---|---|---|
| PVC/OEP | 0.0453 | −1.3439 | 0.000998 | −3.00087 | 1.069712 | 1.157279 |
| PVC/OEC | 0.0453 | −1.3439 | 0.00077 | −3.11351 | 1.233278 | 1.157279 |
| PVC/TBP | 0.0453 | −1.3439 | 0.000847 | −3.07212 | 1.128543 | 1.157279 |
| PMMA/OEP | 0.102 | −0.9914 | 0.00135 | −2.86967 | 1.200915 | 1.393022 |
| PMMA/OEC | 0.102 | −0.9914 | 0.00107 | −2.97062 | 1.376171 | 1.393022 |
| PMMA/TBP | 0.102 | −0.9914 | 0.00265 | −2.57675 | 1.623905 | 1.393022 |
| EX23/OEP | 0.27 | −0.5686 | 0.00261 | −2.58336 | 1.487222 | 1.675753 |
| EX23/OEC | 0.27 | −0.5686 | 0.00229 | −2.64016 | 1.706623 | 1.675753 |
| EX23/OEC | 0.27 | −0.5686 | 0.00272 | −2.56543 | 1.781356 | 1.675753 |
| EX45/OEP | 0.38 | −0.4202 | 0.004427 | −2.35389 | 1.716691 | 1.775012 |
| EX45/OEC | 0.38 | −0.4202 | 0.00261 | −2.58336 | 1.763428 | 1.775012 |
| EX46/OEP | 0.54 | −0.2676 | 0.00493 | −2.30715 | 1.763428 | 1.877073 |
| EX46/0EC | 0.54 | −0.2676 | 0.00399 | −2.39903 | 1.94776 | 1.877073 |
| CA/OEP | 0.78 | −0.1079 | 0.0088 | −2.05552 | 2.015064 | 1.983876 |
| CA/OEC | 0.78 | −0.1079 | 0.00395 | −2.4034 | 1.943385 | 1,983876 |
| CA/TBP | 0.78 | −0.1079 | 0.00859 | −2.0660 | 2.134653 | 1.983876 |
| CA/Ru(II) | 0.78 | −0.1079 | 0.000991 | −3.00393 | 2.22522 | 1.983876 |
| PS/OEP | 2.63 | 0.4199 | 0.01241 | −1.90623 | 2.164353 | 2.336894 |
| PS/OEC | 2.63 | 0.4199 | 0.00805 | −2.0942 | 2.252583 | 2.336894 |
| PS/TBP | 2.63 | 0.4199 | 0.0148 | −1.82974 | 2.370921 | 2.336894 |
| PS/OEPK | 2.63 | 0.4199 | 0.021141 | −1.67487 | 2.505582 | 2.336894 |
| PS/Ru(II) | 2.63 | 0.4199 | 0.00147 | −2.83268 | 2.396465 | 2.336894 |
| PN/OEP | 5.6 | 0.6989 | 0.0175 | −1.75696 | 2.313619 | 2.52349 |
| EX41/OEC | 5.6 | 0.7481 | 0.0338 | −1.47108 | 2.875704 | 2.556406 |
| EX41/Ru(II) | 5.6 | 0.7481 | 0.001926 | −2.71534 | 2.513804 | 2.556406 |
| EX42/OEP | 8 | 0.9031 | 0.0231 | −1.63639 | 2.434193 | 2.659999 |
| ACR1/Ru(II) | 11.4 | 1.0569 | 0.003852 | −2.41431 | 2.814834 | 2.762866 |
| ACR2/Ru(II) | 29 | 1.4623 | 0.0059 | −2.22915 | 3.0 | 3.034048 |
| ACR3/OEP | 34 | 1.5314 | 0.080192 | −1.09587 | 2.974712 | 3.080247 |
| ACR4/OEP | 58 | 1.7634 | 0.127189 | −0.89555 | 3.175030 | 3.235368 |
| PS121/OEP | 100 | 2 | 0.263 | −0.58004 | 3.490537 | 3.39358 |
| SILOX/OEP | 605 | 2.7817 | 0.793 | −0.10073 | 3.969854 | 3.916395 |

Regression Output

| | | | |
|---|---|---|---|
| Constant | 2.05604 | X Coefficient(s) | 0.66877 |
| Std Err of Y Est | 0.134349 | Std Err of Coef. | 0.023462 |
| | | R Squared | 0.96325 |

Figure 8:
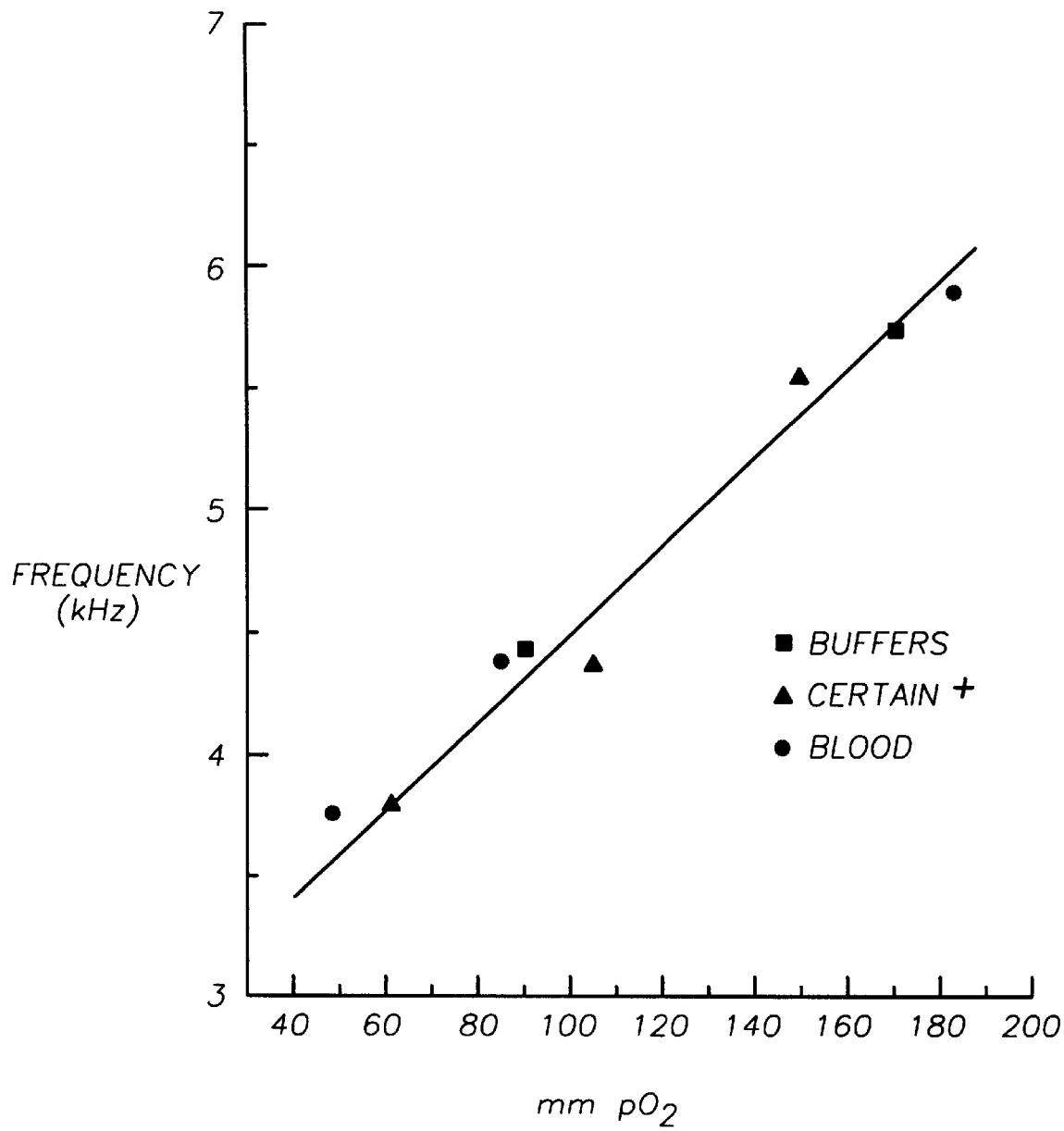
FIG. 8 is a plot of the response to calibrants and blood samples of a polymeric sensing membrane in accordance with the present invention.

Using the above approach, a series of oxygen sensing polymeric membranes with differing permeabilities was examined, and a composite acrylate was determined to match to the permeability needed to satisfy a $k_{SV}$ of 0.0083 with the dye octaethyl-Pt-porphyrin. FIG. 8 shows the measured frequency response signal as a function of partial pressure of oxygen after a continuous exposure to well over 2800 aqueous samples over a four day period. The exhibited samples include tonometered liquid buffers, the QC material Certain Plus™ (available from Ciba Corning Diagnostics Corp.) and tonometered blood samples. The plot shown in FIG. 8 demonstrates the linear relationship between the frequency measured and the partial pressure of oxygen.

The following illustrative and nonlimiting examples are intended to demonstrate certain aspects of the present invention. It is to be understood that these examples should not be construed as limiting.

19

EXAMPLE 1

In certain applications, the dynamic range of pressures of a particular gas to be measured may be known and the temperature at which the measurement is to be made may also be known. Moreover, it may be desirable that a particular fluorescent dye molecule and a particular illumination source be used. For example, given the need to monitor oxygen partial pressures in the range of 400 to 600 mmHg $pO_2$ at 23° C. and the availability of a tris (1,10-phenanthroline)-ruthenium(II) compound (synthesized in accordance with the methods disclosed in *J.A.C.S.* 93, 3184(1971) for use with a Nichia blue LED (purchased from Quantum Devices and emitting at 450 nm) the Stern-Volmer constant for the required dynamic range is 0.002 $(mmHg)^{-1}$ which gives an ideal permeability of 5.25 Barrers. Accordingly, a polymeric material was designed to have a permeability of approximately 5.25 Barrers. The starting materials of the polymeric material comprised, by weight, 55% acrylonitrile, 10% 2-ethylhexylmethacrylate, 10% methylmethacrylate, 15% dodecylmethacrylate, and 10% vinylacetate, and the polymeric material was synthesized in accordance with the methods disclosed in U.S. Pat. No. 5,387,329. This polymeric material had a measured permeability of 5.6 Barrers.

A polymeric sensing membrane was constructed by dissolving 100 mg of the above-described polymeric material and 2 mg of tris (1,10-phenanthroline)-ruthenium (II) complex into 1 g of THF. A glass cover slip which was cleaned and coated with a hydrophobic silane (Glassclad™) served as the substrate material. The solution was spin coated on the glass slide at 2,000 rpm for 20 seconds using a model P6204 precision spin coating system (purchased from Specialty Coating Systems, Inc.) and allowed to dry overnight. The measured Stern-Volmer response to partial pressures of oxygen was observed to be $k_{SV}=0.0019$ $(mmHg)^{-1}$.

EXAMPLE 2

Given the need to measure partial pressures of oxygen in aqueous samples in the range of 0 to 130 mmHg $pO_2$ at 23° C., the requirement to use only a commercially available polymer polystyrene with a permeability of 2.53 Barrers (as reported in the *Polymer Handbook,* third edition) and the requirement to employ an LED source, the theoretical Stern-Volmer constant is $k_{SV}=0.015$ $(mmHg)^{-1}$. For such a case, a fluorescent dye molecule with a relaxation time of approximately 70 seconds may be used. Tetrabenzyl-Pt-porphyrin (synthesized according to methods disclosed in *Journal of the American Chemical Society* 104, 6278 (1982)) has a relaxation time of approximately 63 $\mu$seconds and is excitable around 600 nm. Thus, 100 mg of polystyrene and 1 mg of tetrabenzyl-Pt-porphyrin were solvated in 1 gram of THF. The solution was spin coated on a hydrophobic glass substrate as described in Example 1 and cured in a Heraeus Type VT5042 vacuum oven for one hour at 110° C. The Stern-Volmer constant of the polymeric sensing membrane was 0.014 $(mmHg)^{-1}$, and the membrane was excitable with a yellow (580 nm) LED.

EXAMPLE 3

Before testing the sensitivity of a commercial oxygen sensing membrane from the Joanneum Institute, Graz, a knowledge of the most useful working range was desired for the combination octaethyl-Pt-porphyrin keton dye and polystyrene polymer. A $\tau_O=66$ $\mu$seconds was measured with a Perkin Elmer LS-50B Spectrofluorimeter adjusted for excitation at the 588 nm absorbance band. The resultant MRP calculated from equation (15), (16) and the data of FIG. 7. was found to be 71 mmHg $pO_2$. Thus, a dynamic range of oxygen partial pressures between 0 to 140 mmHg $pO_2$ would make best use of the polymeric sensing membrane's sensitivity when used in conjunction with a yellow (580 nm) LED source.

EXAMPLE 4

For measurements over a dynamic range of 0 to 15 mmHg $pO_2$, at 23° C. in near anaerobic fermentations, the dye octaethyl-Pt-porphyrin can be used with a 555 nm emitting green LED. The octaethyl-Pt-porphyrin was synthesized as described in J. Molecular Spectroscopy (35:3) p359–375 (1970). A theoretical permeability of 50.4 Barrers was required to meet the $k_{SV}=0.133$ $(mmHg)^{-1}$ based on a $\tau_O=85$ $\mu$seconds as measured with a Perkin Elmer LS-50B Spectrofluorimeter. A copolymer having starting material which comprised 60% methacryloxypropyl tris(trimethylsiloxy) silane, 10% 2,2,2-trifluoroethyl methacrylate, 20% ethylmethacrylate and 10% vinyl acetate has a permeability of 58 Barrers and may be used for this application. Approximately 100 mg of the polymeric material was diluted into 1.0 ml of toluene containing 1 mg of the octaethyl-Pt-porphyrin. The solution mixture was spin cast onto a clean glass slide at 2000 rpm for 20 seconds as described in Example 1 and allowed to cure at room temperature for at least 24 hours. The Stern-Volmer constant of the polymeric sensing membrane was 0.127 $(mmHg)^{-1}$.

EXAMPLE 5

For measuring oxygen in blood in the range between 40 to 200 mmHg $pO_2$ ($k_{SV}=0.083$ $(mmHg)^{-1}$) at 37° C. using a green LED, which emits at 555 nm to excite the dye octaethyl-Pt-porphyrin ($\tau_O=85$ $\mu$sec), a polymeric material having a permeability of 0.79 Barrers was needed to optimize the membrane's sensitivity.

A polymer having starting material which comprised 25% acrylonitrile, 10% 2-ethylhexalmethacrylate, 40% methylmethacrylate and 25% vinylacetate was synthesized as follows. 9.46 g acrylonitrile having a molecular weight of 53.06, 13.12 g 2-ethylhexylacrylate having a molecular weight of 184.28, 28.56 g methylmethacrylate having a molecular weight of 100.00, 15.33 g vinyl acetate having a molecular weight of 86.09 and 0.070 g of the initiator azo-bisisobutyronitrile having a molecular weight of 192.3 were dissolved to form a solution. The starting solid materials were recrystalized and the solvents freshly distilled to ensure purity. Two glass plates, each with a sealing rubber gasket along three edges, were mounted parallel to one another and separated by a space of 2 mm. The form was then filled with about 32 g of the above solution and heated to 60° C. for 42 hours in a dry box flushed with nitrogen. The mixture was polymerized to a solid state then dissolved in 150 ml of chloroform. It was subsequently filtered through a glass filter, and precipitated into 4 liters of methanol. The precipitated polymer was then dried in a vacuum for 3 days at 40° C. The membrane, formed from this polymer, had a measured permeability of 0.68 to –0.7 Barrers at 37° C. Into 1 g of THF, 100 mg of the polymeric material and 2 mg of octaethyl-Pt-porphyrin were dissolved, and the solution was spin cast onto a hydrophobic glass substrate surface as in Example 1. The polymeric sensing membrane was cured in a vacuum oven for one hour at 65° C. The measured Stern-Volmer response was 0.0079 $mm^{-1}$ at 37° C.

EXAMPLE 6

For measuring oxygen in a range between 0 to 500 mmHg $pO_2$ with a $k_{SV}=0.004$ $(mmHg)^{-1}$, using a green LED to excite octaethyl-Pt-porphyrin, a polymeric material with a permeability of 0.27 Barrers optimizes the membrane's sensitivity.

A copolymer was synthesized from 50% acrylonitrile, 10% 2-ethylhexalmethacrylate and 40% methylmethacrylate using methods in accordance with U.S. Pat. No. 5,387,329 and had a permeability of 0.27 Barrers. To construct a sensing membrane, the dye and polymer were combined and spin cast by the method described in example 5 except that the cure condition in the vacuum oven was for 1 hour at 75° C. The membrane had a Stern-Volmer constant of 0.00417 $(mmHg)^{-1}$.

EXAMPLE 7

For measuring oxygen in a range between 0 to 900 mmHg $pO_2$ with a $k_{SV}$=0.0022 $(mmHg)^{-1}$, using a yellow LED (580 nm) and octaethyl-Pt-chlorin (absorbance peak at 596 nm and a $\tau_O$=45 μsec), a polymeric material having a permeability of 0.28 Barrers optimizes the membrane's sensitivity. The dye (1 mg) was dissolved in 1 g THF and mixed with 100 mg of the same polymer described in example 6. A sensing membrane was spin cast on a glass slide and cured in a vacuum oven for 1 hour at 75° C. The membrane had a Stern-Volmer constant of 0.0023 $(mmHg)^{-1}$.

Having thus described certain embodiments of the invention, various alterations, modifications and improvements will readily occur to those skilled in the art. Such alterations, modifications and improvements are intended to be part of this disclosure, and are intended to be within the spirit and scope of the invention. The materials employed, as well as their shapes and dimensions, may be altered. In addition, while the use of polymeric sensing membranes in measuring oxygen concentration has been emphasized herein, it is to be understood that the present invention may be utilized in the measurement of the concentration of any gas so long as appropriate polymeric materials and fluorescent dye materials as described herein can be designed and/or employed. Accordingly, the foregoing description is by way of example only and is not intended as limiting. The invention is limited only as defined in the following claims and the equivalents thereto.

What is claimed is:

1. A method of forming a polymeric sensing membrane having a Stern-Volmer constant $k_{SV}$ in the range of about 0.002 $(mmHG)^{-1}$ to 1.0 $(mmHg)^{-1}$, said method comprising the steps of:

using a first selecting step selected from the group consisting of
   a) selecting a fluorescent dye molecule having a relaxation time $\tau_O$, said fluorescent dye molecule capable of emitting fluorescence, wherein oxygen to be sensed by said polymeric sensing membrane is capable of collisionally quenching said fluorescence of said fluorescent dye molecule; or
   b) selecting a polymer having a permeability ($Perm_{O2}$); using a second selecting step selected from the group consisting of
   c) selecting a polymer having a permeability ($Perm_{O2}$) wherein said $Perm_{O2}$ required to provide said Stern-Volmer constant $k_{SV}$ is determined by the mathematical function log $(k_{SV}/\tau_O)$=log $(4\pi \cdot N_A \cdot p)$+log $(Perm_{O2})$, or by the function log $(k_{SV}/\tau_O)$=2.05604+0.66877 log $(Perm_{O2})$, wherein said first selecting step is step a); or
   d) selecting a fluorescent dye molecule having a relaxation time $\tau_O$, wherein said relaxation time $\tau_O$ is determined by the mathematical function log $(k_{SV}/\tau_O)$=log $(4\pi \cdot N_A \cdot p)$+log $(Perm_{O2})$, or by the function log $(k_{SV}/\tau_O)$=2.05604+0.66877 log $(Perm_{O2})$, said fluorescent dye molecule capable of emitting fluorescence, wherein oxygen to be sensed by said polymeric sensing membrane is capable of collisionally quenching said fluorescence of said fluorescent dye molecule, and wherein said first selecting step is step b);

admixing said fluorescent dye molecule with said polymer to form a mixture; and forming said mixture into said polymeric sensing membrane.

2. The method of claim 1, wherein said step of forming said mixture into said polymeric sensing membrane results in a polymeric sensing membrane having a Stern-Volmer constant of from in the range of approximately 0.007 $(mmHg)^{-1}$ to approximately 0.011 $(mmHg)^{-1}$.

3. The method of claim 1, wherein said step of forming said mixture into said polymeric sensing membrane results in a polymeric sensing membrane having a Stern-Volmer constant in the range of approximately 0.002 $(mmHg)^{-1}$ to approximately 0.005 $(mmHg)^{-1}$.

4. The method of claim 1, wherein said step of forming said mixture into said polymeric sensing membrane results in a polymeric sensing membrane having a Stern-Volmer constant in the range of approximately 0.2 $(mmHg)^{-1}$ to approximately 1.0 $(mmHg)^{-1}$.

5. The method of claim 2, wherein said first selecting step is step a).

6. The method of claim 2, wherein said first selecting step is step b).

7. The method of claim 2, wherein said fluorescent dye molecule has a relaxation time of from approximately 45 microseconds to approximately 120 microseconds.

8. The method of claim 2, wherein said fluorescent dye molecule has a relaxation time of from approximately 1 microsecond to approximately 45 microseconds.

9. The method of claim 2, wherein said polymer has a permeability of from approximately 0.47 Barrers to approximately 2.05 Barrers.

10. The method of claim 2, wherein said polymer has a permeability of from approximately 2.05 Barrers to approximately 611 Barrers.

11. The method of claim 2, wherein said fluorescent dye molecule is selected from the group consisting of platinum porphyrins, platinum chlorins, and ruthenium complexes.

12. The method of claim 2, wherein said fluorescent dye is a platinum porphyrin.

13. The method of claim 2, wherein said fluorescent dye is octaethyl-Pt-porphyrin.

14. The method of claim 2, wherein said fluorescent dye is tetrabenzyl-Pt-porphyrin.

15. The method of claim 2, wherein said polymer comprises at least one polymeric material selected from the group consisting of polystyrenes, polyalkanes, polymethacrylates, polynitriles, polyvinyls, polydienes, polyesters, polycarbonates, polysiloxanes, polyamides, polyacetates, polyimides, polyurethanes, celluloses and derivatives thereof.

16. The method of claim 13, wherein said polymer comprises at least one polymeric material selected from the group consisting of polymethacrylates, polyacetates and polynitriles.

17. The method of claim 14, wherein said polymer comprises at least one polymeric material selected from the group consisting of polymethacrylates, polyacetates and polynitriles.

18. The method of claim 1, wherein said steps of admixing said fluorescent dye molecule with said polymer and forming said mixture into said polymeric membrane further include:
   dissolving said fluorescent dye molecule and said polymer in a solvent to form said mixture; and
   disposing said mixture on an optically clear substrate to form an optical sensor.

19. The method of claim 18, wherein said step of dissolving said fluorescent dye molecule and said polymer in a solvent further includes dissolving said fluorescent dye molecule and said polymer in a solvent selected from the group consisting of THF, chloroform, and toluene.

20. The method of claim 1, wherein said polymer is substantially free of leachable plasticizers.

* * * * *